(12) United States Patent
Adjei et al.

(10) Patent No.: US 12,128,042 B2
(45) Date of Patent: Oct. 29, 2024

(54) TAMPER RESISTANT IMMEDIATE RELEASE FORMULATIONS

(71) Applicant: Rhodes Pharmaceuticals L.P., Coventry, RI (US)

(72) Inventors: Akwete L. Adjei, East Greenwich, RI (US); Sibao Chen, Warwick, RI (US); Robert J. Kupper, Warwick, RI (US); Vincent Mancinelli, Scituate, RI (US)

(73) Assignee: Rhodes Pharmaceuticals L.P., Coventry, RI (US)

( * ) Notice: Subject to any disclaimer, the term of this patent is extended or adjusted under 35 U.S.C. 154(b) by 389 days.

(21) Appl. No.: 17/501,641

(22) Filed: Oct. 14, 2021

(65) Prior Publication Data
US 2022/0031693 A1 Feb. 3, 2022

Related U.S. Application Data

(63) Continuation of application No. 14/377,900, filed as application No. PCT/IB2013/000444 on Mar. 1, 2013, now Pat. No. 11,173,155.

(60) Provisional application No. 61/724,141, filed on Nov. 8, 2012, provisional application No. 61/606,156, filed on Mar. 2, 2012.

(51) Int. Cl.
| | | |
|---|---|---|
| A61K 31/485 | (2006.01) | |
| A61K 9/16 | (2006.01) | |
| A61K 9/20 | (2006.01) | |
| A61K 9/28 | (2006.01) | |
| A61K 9/50 | (2006.01) | |
| A61K 45/06 | (2006.01) | |

(52) U.S. Cl.
CPC .......... *A61K 31/485* (2013.01); *A61K 9/1635* (2013.01); *A61K 9/1676* (2013.01); *A61K 9/1682* (2013.01); *A61K 9/2018* (2013.01); *A61K 9/2054* (2013.01); *A61K 9/2077* (2013.01); *A61K 9/2081* (2013.01); *A61K 9/2095* (2013.01); *A61K 9/2846* (2013.01); *A61K 9/2853* (2013.01); *A61K 9/5078* (2013.01); *A61K 45/06* (2013.01)

(58) Field of Classification Search
None
See application file for complete search history.

(56) References Cited

U.S. PATENT DOCUMENTS

| | | |
|---|---|---|
| 4,070,494 A | 1/1978 | Hoffmeister et al. |
| 5,965,161 A | 10/1999 | Oshlack |
| 6,455,557 B1 | 9/2002 | Pellegrini et al. |
| 6,740,341 B1 | 5/2004 | Holt et al. |
| 8,999,961 B2 | 4/2015 | Wright et al. |
| 2003/0068375 A1 | 4/2003 | Wright et al. |
| 2004/0091544 A1 | 5/2004 | Ruff et al. |
| 2005/0112195 A1 | 5/2005 | Cruz et al. |
| 2006/0210630 A1 | 9/2006 | Liang et al. |
| 2007/0264327 A1 | 11/2007 | Kumar et al. |
| 2008/0057122 A1 | 3/2008 | Toney-Parker et al. |
| 2008/0063725 A1 | 3/2008 | Guimberteau et al. |
| 2008/0152595 A1 | 6/2008 | Emigh et al. |
| 2009/0022798 A1 | 1/2009 | Rosenberg et al. |
| 2010/0099696 A1 | 4/2010 | Soscia |

FOREIGN PATENT DOCUMENTS

| | | |
|---|---|---|
| EP | 1 967 183 | 10/2008 |
| WO | 2004067039 | 8/2004 |
| WO | 2004069135 | 8/2004 |
| WO | 2005046684 | 5/2005 |
| WO | 2006124890 | 11/2006 |
| WO | 2007120135 | 10/2007 |
| WO | 2008012474 | 1/2008 |
| WO | 2010044842 | 4/2010 |
| WO | 2010066034 | 6/2010 |
| WO | 2010069050 | 6/2010 |
| WO | 2011/041414 | 4/2011 |
| WO | 2011051155 | 5/2011 |
| WO | 2013038267 | 3/2013 |

OTHER PUBLICATIONS

Al-Taani, et al., Effect of Microenviornment pH of Swellable and Erodable Buffered Matrices on the Release haracteristics of Diclofenac Sodium, AAPS PharmSciTech, 2003, pp. 1-6, vol. 4, No. 3, Article 43, Jordan University of Science and Technology, Irbid, Jordan.

Aslani, et al., Effect of gelation conditions and dissolution media on the release of paracetamol from alginate gel beads, Journal of Microencapsulation, 1996, pp. 601-614, vol. 13, No. 5, Taylor & Francis Ltd., United Kingdom.

Heinze, Thomas, Carboxymethyl Ethers of Cellulose and Startch—A Review, Center of Excellence for Polysaccharide Research, 2005, pp. 13-29, No. 3, Friedrich Schiller University of Jena, Jena, Germany.

Kohane, et al., pH-Triggered Release of Macromolecules from Spray-Dried Polymethacrylate Microparticles, Pharmaceutical Research, Oct. 2003, pp. 1533-1538, vol. 20, No. 10, Plenum Publishing Corporation, New York, NY.

International Search Report for PCT/IB2013/000444, dated Sep. 4, 2013, 4 pages.

Oxecta® CDER (FDA) Pharmacology & Toxicology Review, 35 pgs., 2011.

"Chitosan," Handbook of Pharmaceutical Excipients, 4th Edition, 2003, pp. 132-135.

(Continued)

*Primary Examiner* — Tigabu Kassa
(74) *Attorney, Agent, or Firm* — Lowenstein Sandler LLP

(57) ABSTRACT

Disclosed in certain embodiments is an immediate release solid oral dosage form comprising a plurality of particles, each particle comprising: (i) a core comprising a first active agent; (ii) a coating comprising a second active agent layered over the core; and (iii) a material that is sensitive to acidic pH layered over the coated core; wherein the dosage form releases at least about 70% of the second active agent within 45 minutes as measured by in-vitro dissolution in a USP Apparatus 2 (paddle) at 50 rpm in 500 ml 0.1 N HCl at 37° C.

23 Claims, 11 Drawing Sheets

(56) References Cited

OTHER PUBLICATIONS

"Crospovidone," Handbook of Pharmaceutical Excipients, 4th Edition, 2003, pp. 184-185.
Eudragit, Evonik Industries Brochure pp. 3-15, 2010.
Moorman-Li, et al., "A Review of Abuse-Deterrent Opioids For Chronic Nonmalignant Pain," Jul. 2012, pp. 412-418, vol. 37, No. 7.
"Oxecta," Clinial Pharmacology and Biopharmaceutics Review(s), May 16, 2011, 62 pgs.
"Polacrilin Potassium," Handbook of Pharmaceutical Excipients, 4th Edition, 2003, pp. 444-445.
"Starch, Pregelatinized," Handbook of Pharmaceutical Excipients, 4th Edition, 2003, pp. 609-611.
"SWELSTAR Pregelatinized Starch NF PD-1 (Disintegrant) from Asahi Kasei," American Pharmaceutical Review, Sep. 10, 2017, 2 pgs.
Notice of Opposition, Facts and Arguments in accordance with Rule 76(2)(c) EPC, 12 p. 2002.

Human Bioavailability Results: Mean (SD) Plasma Oxycodone Concentration-Time Profile (Linear Scale) – Fed PK Summary (E PO vs RLD)

Stage Layering of Naloxone on Substrate APAP Granules

Processing Stage II - Production of Naloxone Loaded Polymer Coated Pellets

TAMPER RESISTANT IMMEDIATE RELEASE FORMULATIONS

CROSS REFERENCE TO RELATED APPLICATIONS

This application is a continuation of U.S. Non Provisional patent application Ser. No. 14/377,900 filed on Aug. 11, 2014, which is a national phase entry of International Application No. PCT/IB2013/000444 filed on Mar. 1, 2013, which claims the benefit of U.S. Provisional Patent Application No. 61/606,156 filed on Mar. 2, 2012 and U.S. Provisional Patent Application No. 61/724,141 filed on Nov. 8, 2012. The contents of these applications are hereby incorporated by reference in their entirety.

FIELD OF THE INVENTION

The present invention relates to the field of pharmaceutical dosage forms that are resistant to tampering and abuse.

BACKGROUND

Pharmaceutical products are sometimes the subject of abuse. For example, a particular dose of opioid agonist may be more potent when administered parenterally as compared to the same dose administered orally. Some formulations can be tampered with to provide the opioid agonist contained therein for illicit use. Opioid agonist formulations intended for oral use are sometimes crushed or subject to extraction with solvents (e.g., ethanol) by drug abusers to provide the opioid contained therein for non-prescribed illicit use (e.g., nasal or parenteral administration).

There have previously been attempts in the art to control the abuse potential associated with immediate release opioid analgesics. For example, the combination of pentazocine and naloxone has been utilized in tablets available in the United States, commercially available as Talwin® Nx from Sanofi-Winthrop. Talwin® Nx contains pentazocine hydrochloride equivalent to 50 mg base and naloxone hydrochloride equivalent to 0.5 mg base. Talwin® Nx is indicated for the relief of moderate to severe pain. The amount of naloxone present in this combination has low activity when taken orally, and minimally interferes with the pharmacologic action of pentazocine. However, this amount of naloxone given parenterally has profound antagonistic action to narcotic analgesics. Thus, the inclusion of naloxone is intended to curb a form of misuse of oral pentazocine which occurs when the dosage form is solubilized and injected. Therefore, this dosage has lower potential for parenteral misuse than previous oral pentazocine formulations. A fixed combination therapy comprising tilidine (50 mg) and naloxone (4 mg) has been available in Germany for the management of severe pain since 1978 (Valoron® N, Goedecke). The rationale for the combination of these drugs is effective pain relief and the prevention of tilidine addiction through naloxone-induced antagonisms at the morphine receptor. A fixed combination of buprenorphine and naloxone was introduced in 1991 in New Zealand (Temgesic® Nx, Reckitt & Colman) for the treatment of pain.

There exists a need in the art for an immediate release dosage form containing a drug susceptible to abuse that is resistant to parenteral and nasal abuse. In the case of opioid analgesics, there exists a need for a tamper resistant immediate release formulation that does not solely rely upon the inclusion of an antagonist in the formulation to deter parenteral and nasal abuse.

SUMMARY OF THE INVENTION

It is an object of certain embodiments of the present invention to provide an immediate release solid oral dosage form comprising an active agent (e.g., an opioid analgesic) which is tamper resistant.

It is an object of certain embodiments of the present invention to provide an immediate release solid oral dosage form comprising an active agent (e.g., an opioid analgesic) which is subject to less parenteral abuse than other dosage forms.

It is an object of certain embodiments of the present invention to provide an immediate release solid oral dosage form comprising an active agent (e.g., an opioid analgesic) which is subject to less intranasal abuse than other dosage forms.

It is a further object of certain embodiments of the present invention to provide an immediate release solid oral dosage form comprising an active agent (e.g., an opioid analgesic) which is subject to less diversion than other dosage forms.

It is a further object of certain embodiments of the present invention to treat a disease or condition (e.g., pain) in human patients by administering an immediate release solid oral dosage form as disclosed herein to a patient in need thereof.

It is a further object of certain embodiments of the present invention to provide a method of treating pain in human patients with an immediate release solid oral dosage form comprising an opioid analgesic while reducing the abuse potential of the dosage form.

It is a further object of certain embodiments of the present invention to provide a method of manufacturing an immediate release solid oral dosage form of an active agent (e.g., an opioid analgesic) as disclosed herein.

It is a further object of certain embodiments of the present invention to provide a use of a medicament (e.g., an opioid analgesic) in the manufacture of a tamper-resistant dosage form as disclosed herein for the treatment of a disease state (e.g., pain).

The above objects of the present invention and others can be achieved by the present invention, which in certain embodiments is directed to an immediate release solid oral dosage form comprising a plurality of particles, each particle comprising (i) an active agent; and (ii) a material that is sensitive to acidic pH; wherein the dosage form releases at least about 70% of the active agent within 45 minutes as measured by in-vitro dissolution in a USP Apparatus 2 (paddle) at 50 rpm in 500 ml 0.1N HCl at 37° C.

In certain embodiments, the material that is sensitive to acidic pH is less soluble in a pH range of between about 6 and about 8.5 than a pH range of between about 1 and about 5.

In certain embodiments, the plurality of particles are dispersed in a matrix and compressed into a tablet or contained within a pharmaceutically acceptable capsule. The matrix can contain at least one of a gelling agent, a disintegrant or a filler.

In certain embodiments, the solid oral dosage form disclosed herein releases at least about 70% by weight, or at least about 75% by weight, or at least about 80% by weight, or at least about 85% by weight, or at least about 90% by weight, or at least about 95% by weight of the drug (e.g., opioid agonist) within 45 minutes as measured by in-vitro dissolution in a USP Apparatus 2 (paddle) at 50 rpm in 500 ml 0.1N HCl at 37° C.

In certain embodiments, the solid oral dosage form disclosed herein releases at least about 85% by weight, at least about 90% by weight, or at least about 95% by weight, or at least about 98% by weight of the drug (e.g., opioid agonist) within 60 minutes as measured by in-vitro dissolution in a USP Apparatus 2 (paddle) at 50 rpm in 500 ml 0.1N HCl at 37° C.

In other embodiments, the viscosity resulting from mixing a unit dose of the dosage form with from about 0.5 to about 10 ml of distilled water prevents or reduces the ability of the drug (e.g., opioid agonist) from being drawn up into a syringe, or from being systemically absorbed, when administered by the parenteral or nasal route.

In embodiments with a first and second active agent, the viscosity resulting from mixing a unit dose of the dosage form with from about 0.5 to about 10 ml of distilled water prevents or reduces the ability of the first active agent, the second active agent, or both agents from being drawn up into a syringe, or from being systemically absorbed, when administered by the parenteral or nasal route.

In certain embodiments, the present invention is directed to an immediate release solid oral dosage form comprising a plurality of particles, each particle comprising (i) an opioid agonist; and (ii) a material that is sensitive to acidic pH; wherein the plurality of particles are dispersed in a matrix comprising (i) a gelling agent; and (ii) an optional disintegrant; wherein the dosage form releases at least about 70% of the opioid agonist within 45 minutes as measured by in-vitro dissolution in a USP Apparatus 2 (paddle) at 50 rpm in 500 ml 0.1N HCl at 37° C.; and wherein the viscosity of the dosage form mixed with from about 0.5 to about 10 ml of distilled water prevents or reduces the ability of the opioid agonist from being drawn up into a syringe, or from being systemically absorbed, when administered by the parenteral or nasal route.

In certain embodiments, the present invention is directed to immediate release solid oral dosage forms comprising more than one active agent. By way of example, such an immediate release solid oral dosage form may comprise a plurality of particles, each particle comprising (i) a core comprising a first active agent; (ii) a coating comprising a second active agent layered over the core; and (iii) a material that is sensitive to acidic pH layered over the coated core; wherein the dosage form releases at least about 70% of the first active agent, the second active agent or both active agents, within 45 minutes as measured by in-vitro dissolution in a USP Apparatus 2 (paddle) at 50 rpm in 500 ml 0.1N HCl at 37° C. Contemplated active agent combinations include, but are not limited to, opioid analgesics and non-opioid analgesics. Exemplary combinations include oxycodone or a pharmaceutically acceptable salt thereof and acetaminophen; oxycodone or a pharmaceutically acceptable salt thereof and aspirin; oxycodone or a pharmaceutically acceptable salt thereof and ibuprofen; hydrocodone or a pharmaceutically acceptable salt thereof and acetaminophen; and hydrocodone or a pharmaceutically acceptable salt thereof and ibuprofen.

In certain embodiments, the present invention is directed to a solid oral dosage form comprising a plurality of particles, each particle comprising (i) an opioid agonist; and (ii) a material that is sensitive to acidic pH; wherein the plurality of particles are dispersed in a matrix comprising a gelling agent; and a disintegrant; wherein the dosage form releases at least about 70% of the opioid agonist within 45 minutes as measured by in-vitro dissolution in a USP Apparatus 2 (paddle) at 50 rpm in 500 ml 0.1N HCl at 37° C.; and wherein the viscosity of the dosage form mixed with from about 0.5 to about 10 ml of distilled water prevents the opioid agonist from being systemically absorbed, or reduces the ability of the opioid agonist to be systemically absorbed, when administered by the parenteral or nasal route.

In certain embodiments, the present invention is directed to a solid oral dosage form comprising a plurality of particles, each particle comprising (i) a core comprising a first active agent (e.g., a non-opioid analgesic such as acetaminophen, ibuprofen or aspirin); (ii) a coating comprising a second active agent (e.g., an opioid agonist such as oxycodone, hydrocodone or a pharmaceutically acceptable salt thereof) layered over the core; and (iii) a material that is sensitive to acidic pH layered over the coated core; wherein the plurality of particles are dispersed in a matrix comprising a gelling agent; and a disintegrant; wherein the dosage form releases at least about 70% of the opioid agonist within 45 minutes as measured by in-vitro dissolution in a USP Apparatus 2 (paddle) at 50 rpm in 500 ml 0.1N HCl at 37° C.; and wherein the viscosity of the dosage form mixed with from about 0.5 to about 10 ml of distilled water prevents the opioid agonist from being systemically absorbed, or reduces the ability of the opioid agonist to be systemically absorbed, when administered by the parenteral or nasal route.

In certain embodiments, the present invention is directed to a process for preparing an immediate release solid oral dosage form comprising (i) preparing a plurality of particles, each particle comprising an active agent and a material that is sensitive to acidic pH; and (ii) dispersing the plurality of particles into a matrix; wherein the dosage form releases at least about 70% of the active agent within 45 minutes as measured by in-vitro dissolution in a USP Apparatus 2 (paddle) at 50 rpm in 500 ml 0.1N HCl at 37° C.

In certain embodiments, the present invention is directed to a process for preparing an immediate release solid oral dosage form comprising (i) granulating an active agent and a material that is sensitive to acidic pH to obtain a granulation; (ii) compressing the granulation into a tablet or containing the granulation in a capsule; wherein the dosage form releases at least about 70% of the active agent within 45 minutes as measured by in-vitro dissolution in a USP Apparatus 2 (paddle) at 50 rpm in 500 ml 0.1N HCl at 37° C.

In certain embodiments, the present invention is directed to a process for the preparation of a dosage form as disclosed herein that releases at least about 70% by weight, or at least about 75% by weight, or at least about 80% by weight, or at least about 85% by weight, or at least about 90% by weight, or at least about 95% by weight of the drug (e.g., opioid agonist) within 45 minutes as measured by in-vitro dissolution in a USP Apparatus 2 (paddle) at 50 rpm in 500 ml 0.1N HCl at 37° C.

In certain embodiments, the present invention is directed to a process for the preparation of a solid oral dosage form as disclosed herein that releases at least about 85% by weight, or at least about 90% by weight, or at least about 95% by weight, or at least about 98% by weight of the drug (e.g., opioid agonist) within 60 minutes as measured by in-vitro dissolution in a USP Apparatus 2 (paddle) at 50 rpm in 500 ml 0.1N HCl at 37° C.

In certain embodiments, the present invention is directed to a process for the preparation of a solid oral dosage form as disclosed herein comprising (a) preparing a plurality of particles, each particle comprising (i) a core comprising a first active agent (e.g., an non-opioid analgesic); (ii) a coating comprising a second active agent (e.g., an opioid analgesic); and (iii) a material that is sensitive to acidic pH layered over the coated core; wherein the dosage form releases at least about 70% of the first active agent, the second active agent or both active agents, within 45 minutes as measured by in-vitro dissolution in a USP Apparatus 2 (paddle) at 50 rpm in 500 ml 0.1N HCl at 37° C.

In other embodiments, the present invention is directed to a process for the preparation of a dosage form as disclosed herein wherein the viscosity resulting from mixing a unit dose of the dosage form (crushed or uncrushed) with from about 0.5 to about 10 ml of distilled water prevents or reduces the ability of the drug (e.g., opioid agonist) from being drawn up into a syringe, or from being systemically absorbed, when administered by the parenteral or nasal route.

In describing the present invention, the following terms are to be used as indicated below. As used herein, the singular forms "a," "an," and "the" include plural references unless the context clearly indicates otherwise. Thus, for example, reference to "an active agent" includes a single active agent as well as a mixture of two or more different active agents, and reference to a "gelling agent" includes a single gelling agent as well as a mixture of two or more different gelling agents, and the like.

As used herein, the terms "active agent," "active ingredient," "pharmaceutical agent," and "drug" refer to any material that is intended to produce a therapeutic, prophylactic, or other intended effect, whether or not approved by a government agency for that purpose. These terms with respect to specific agents include all pharmaceutically active forms of the agent, including the free base form of the agent, and all pharmaceutically acceptable salts, complexes, stereoisomers, crystalline forms, co-crystals, ether, esters, hydrates, solvates, and mixtures thereof, where the form is pharmaceutically active.

As used herein, the terms "therapeutically effective" refers to the amount of drug or the rate of drug administration needed to produce a desired therapeutic result.

As used herein, the terms "prophylactically effective" refers to the amount of drug or the rate of drug administration needed to produce a desired prophylactic result.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is non-superimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "racemic" refers to a mixture of enantiomers.

The term "resolution" refers to the separation or concentration or depletion of one of the two enantiomeric forms of a molecule.

The term "patient" means a subject, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

The term "layered" means being completely or partially coated onto a substrate (e.g., an inert core).

The term "bioavailability" is defined for purposes of the present invention as the relevant extent to which the drug (e.g., oxycodone) is absorbed from the unit dosage forms. Bioavailability is also referred to as AUC (i.e., area under the plasma concentration/time curve).

The term "$C_{max}$" denotes the maximum plasma concentration obtained during the dosing interval.

The term "$T_{max}$" denotes the time to maximum plasma concentration ($C_{max}$).

The term "population of patients" or "population of subjects" or "population of healthy subjects" means that the discussion (or claim) is directed to the mean pharmacokinetic parameters of at least two patients, subjects, or healthy subjects; at least six patients, subjects or healthy subjects; or at least twelve patients, subjects or healthy subjects.

For purposes of the present invention, the formulations disclosed herein are preferably dose proportional. In dose proportional formulations, the pharmacokinetic parameters (e.g., AUC and $C_{max}$) and/or in-vitro release increase linearly from one dosage strength to another. Therefore, the pharmacokinetic and in-vitro parameters of a particular dose can be inferred from the parameters of a different dose of the same formulation.

DETAILED DESCRIPTION

Figure 1:
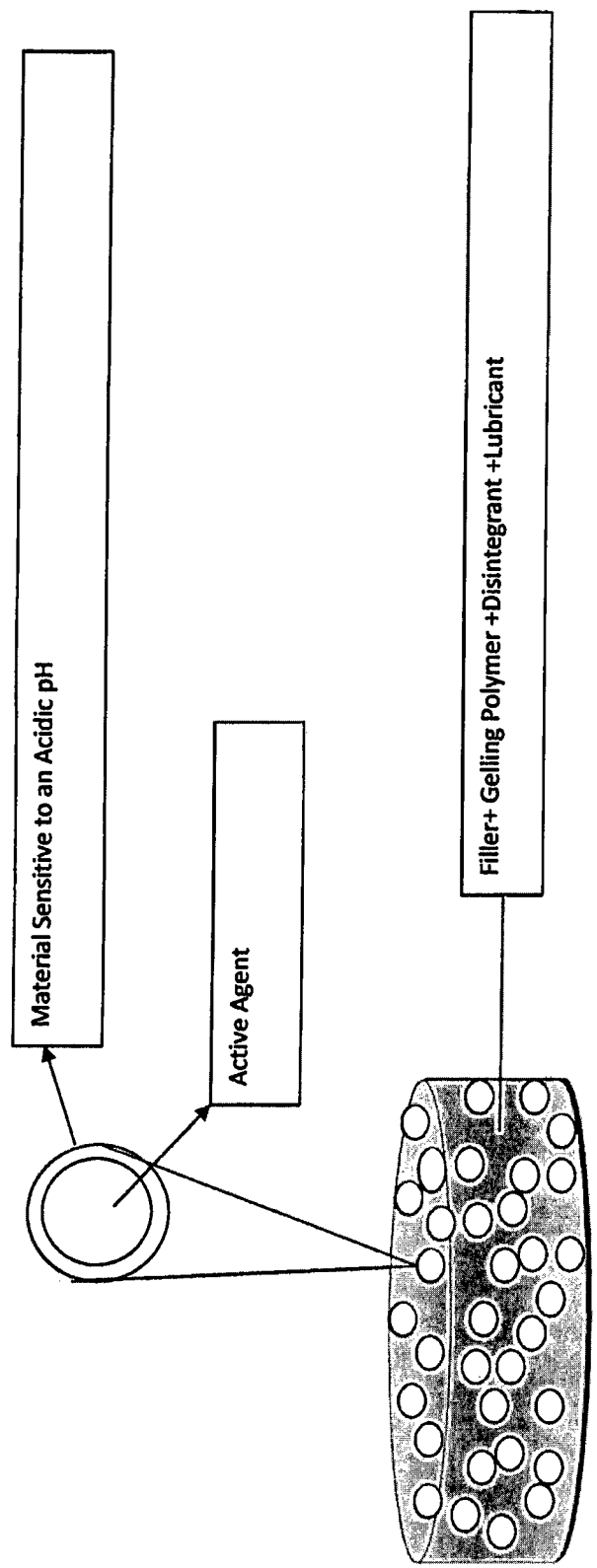
FIG. 1 is a graphical depiction of a formulation according to the present invention.

Particle based formulations of active agents have utilized various materials in order to control the release of the active agent after oral administration. For example, polymer based active agent formulations can be designed to release the active agent over a prolonged period of time or to target the release of the active agent at a specific point in the gastrointestinal system based on a pH dependent differential release.

In addition, gelling agents have been contemplated for use in pharmaceutical formulations in order to deter the abuse of dosage forms containing a drug susceptible to abuse. One form of abuse is the crushing of a controlled release dosage form in order to liberate the drug contained therein for illicit use such as parenteral administration or through absorption across a mucosal surface. When a dosage form having a gelling agent is crushed and then mixed with a solution, a viscosity is obtained which may inhibit the drug from being drawn into a needle, thereby hindering parenteral abuse. Similarly, when the crushed dosage form is applied to a mucosal surface (e.g., the nasal cavity) the composition will gel upon contact with mucosal moisture, thereby inhibiting absorption.

Controlled release dosage forms of drugs of abuse have received considerable attention in an attempt to develop tamper-resistant technologies as the crushing of the dosage form may liberate an amount of active agent normally intended for prolonged release (e.g., 12 to 24 hours).

Immediate release dosage forms are also the subject of abuse and present public safety issues when administered by other than the intended route. One problem to overcome in incorporating a polymer and/or a gelling agent into an immediate release dosage form is controlled release characteristics that such an agent may impart to a dosage form when included in sufficient amounts to inhibit tampering.

In certain situations, an immediate release dosage form can be abused without crushing, e.g., by contacting the intact dosage form with a liquid to dissolve the active agent contained therein. This can be a particular issue with intact immediate release dosage forms that are in particulate form, given the larger surface area and increased dissolution of such dosage forms.

Immediate release dosage forms play a vital role in the management of both acute and chronic conditions (e.g., pain management with opioid analgesics). Therefore, it is important to provide a tamper-resistant dosage form of a drug susceptible to abuse that maintains an immediate release profile. In certain embodiments, the immediate release profile is such that the dosage form releases at least about 70% w/w of the drug within 45 minutes as measured by in-vitro dissolution in a USP Apparatus 2 (paddle) at 50 rpm in 500 ml 0.1N HCl or simulated gastric fluid without enzymes (SGF) at 37° C. In other embodiments, the immediate release profile is such that the dosage form releases at least about 70% w/w of the drug within 45 minutes as measured by in-vitro dissolution in a USP Apparatus 1 (basket) at 50 rpm in 900 ml distilled water at 37° C.

In certain embodiments, the present invention is directed to an immediate release solid oral dosage form comprising a plurality of particles, each particle comprising (i) an active agent; and (ii) a material that is sensitive to acidic pH; wherein the dosage form releases at least about 70% of the active agent within 45 minutes as measured by in-vitro dissolution in a USP Apparatus 2 (paddle) at 50 rpm in 500 ml simulated 0.1N HCl or simulated gastric fluid without enzymes (SGF) at 37° C. Alternatively, such embodiments can release at least about 70% w/w of the drug within 45 minutes as measured by in-vitro dissolution in a USP Apparatus 1 (basket) at 50 rpm in 900 ml distilled water at 37° C.

In certain embodiments, the present invention is directed to an immediate release solid oral dosage form comprising a plurality of particles, each particle comprising (i) an active agent susceptible to abuse (e.g., an opioid agonist); and (ii) a material that is sensitive to acidic pH; wherein the plurality of particles are dispersed in a matrix comprising (i) a gelling agent; and (ii) an optional disintegrant; wherein the dosage form releases at least about 70% of the active agent within 45 minutes as measured by in-vitro dissolution in a USP Apparatus 2 (paddle) at 50 rpm in 500 ml 0.1N HCl or simulated gastric fluid without enzymes (SGF) at 37° C. Alternatively, such embodiments can release at least about 70% w/w of the drug within 45 minutes as measured by in-vitro dissolution in a USP Apparatus 1 (basket) at 50 rpm in 900 ml distilled water at 37° C.

In certain embodiments, the rate of release of the active agent (e.g., opioid agonist) is slower in water as compared to 0.1N HCL. For example, the amount of active agent released at one or more time points selected from 5, 10, 15, 30, 45 or 60 minutes as measured by in-vitro dissolution in a USP Apparatus 2 (paddle) at 50 rpm in 500 ml of distilled water at 37° C. is less than the amount of active agent released at the same time point(s) as measured by in-vitro dissolution in a USP Apparatus 1 (basket) at 50 rpm in 900 ml of 0.1N HCl at 37° C. In certain embodiments the ratio of the amount released in water to the amount released in 0.1N HCl at each of the time point(s) is about 1:10 to less than 1:1; about 1:5 to about 9:10, about 3:10 to about 4:5, or about 2:5 to about 7:10 or about 1:2 to about 3:5. In other embodiments, the ratio is about 1:10, about 9:10, about 3:10, about 9:10, about 1:2, about 9:10, about 7:10; about 9:10 or about 4:5 to about 9:10. In other embodiments, the ratio is about 1:10, about 1:5, about 3:10, about 2:5, about 1:2, about 3:5, about 7:10; about 4:5 or about 9:10.

A unit dose of an immediate release dosage form of the present invention may include without limitation, from about 2 to about 75 particles; from about 10 to about 50 particles; or from about 15 to about 25 particles. In other embodiments, a unit dose of an immediate release dosage form of the present invention may include without limitation, from about 50 to about 500 particles; from about 75 to about 350 particles; from about 100 to about 300 particles; or from about 150 to about 250 particles.

The particles utilized in the present invention may have a mean diameter from about 0.1 mm to about 10 mm; from about 0.5 mm to about 8 mm; from about 1 mm to about 6 mm; or from about 2 mm to about 4 mm.

In certain embodiments comprising a gelling agent, the viscosity of the dosage form (crushed or intact) mixed with from about 0.5 to about 10 ml of distilled water prevents or reduces the ability of the active agent from being drawn up into a syringe, or from being systemically absorbed, when administered by the parenteral or nasal route.

In certain embodiments, with regard to the plurality of particles of the present invention, each particle comprises (i) a core comprising the active agent; and (ii) the material that is sensitive to acidic pH layered on the core. In such embodiments, the core may comprise (i) an inert excipient (e.g., a sugar sphere) layered with the active agent or (ii) the active agent dispersed in a pharmaceutically acceptable excipient. Alternatively, the core can comprise the active agent without an excipient or with minimal excipient.

In other embodiments, with regard to the plurality of particles, each particle comprises (i) a core comprising an inert excipient; and (ii) a coating comprising both the active agent and the material that is sensitive to acidic pH layered on the core.

In further embodiments, with regard to the plurality of particles, each particle comprises the active agent dispersed in the material that is sensitive to acidic pH (e.g., in the form of a blend or a granulation). In such an embodiment, the particle may have an optional coating such as a film coat.

In other embodiments, each core of the plurality of particles can comprise an additional active agent in place of, or in addition to, an inert excipient. For example, a first active agent can be used as a substrate for coating a second active agent thereon. The first active agent can be a substantially pure active pharmaceutical ingredient or can be mixed with a pharmaceutically acceptable excipient prior to coating with the second active agent. The first active agent utilized as a substrate can be in the form of, e.g., a powder or granules. The second active agent can be applied to the first active agent by any means such as spray-coating.

In other embodiments, the core may comprise a first active agent layered onto an inert excipient and the second active agent layered thereon. Alternatively, the first active agent can be dispersed in a pharmaceutically acceptable excipient to form a plurality of substrates and the second active agent can be layered thereon. An optional subcoat of a film forming material (e.g., hydroxypropylmethylcellulose or polyvinyl alcohol) can be layered between the first and second active agent.

In additional embodiments, the core may comprise an inert excipient layered with a coating comprising a mixture of the first active agent and the second active agent. Alternatively, the first active agent and the second active agent can both be dispersed in a pharmaceutically acceptable excipient to form a plurality of substrates and the material sensitive to acidic pH can be layered thereon.

The material that is sensitive to acidic pH of the present invention may be a polymer. In certain embodiments, the polymer is soluble in a pH of between about 1 and about 5. In other embodiments, the polymer is insoluble in a pH of between about 6 and about 8.5. In further embodiments, the polymer is less soluble in a pH range of between about 6 and about 8.5 than in a pH range of between about 1 and about 5.

In certain embodiments, the material that is sensitive to acidic pH provides less dissolution of active agent (e.g., opioid agonist) in an amount of solvent typically used for illicit extraction (e.g., 0.5 to about 10 ml of water) as compared to the dissolution in the gastric system upon administration. This can be tested by in-vitro dissolution in a USP Apparatus 2 (paddle) at 50 rpm in 500 ml of distilled water at 37° C. and an in-vitro dissolution in a USP Apparatus 1 (basket) at 50 rpm in 900 ml of 0.1N HCl at 37° C. The ratio of the amount released in water to the amount released in 0.1N HCl at one or more time points selected from 5, 10, 15, 30, 45 or 60 is about 1:10 to less than 1:1; about 1:5 to about 9:10, about 3:10 to about 4:5, or about 2:5 to about 7:10 or about 1:2 to about 3:5. In other embodiments, the ratio is about 1:10, about 9:10, about 3:10, about 9:10, about 1:2, about 9:10, about 7:10; about 9:10 or about 4:5 to about 9:10. In other embodiments, the ratio is about 1:10, about 1:5, about 3:10, about 2:5, about 1:2, about 3:5, about 7:10; about 4:5 or about 9:10.

The polymer utilized in the present invention can be, e.g., a polyacrylate, a polysaccharide, an ion exchange resin, or a mixture thereof.

An example of a polyacrylate that can be utilized in the present invention is a copolymer comprising amino and/or alkylamino and/or dialkylamino groups such as copolymers comprising methyl methacrylate and diethylaminoethyl methacrylate such as commercially available as Kollicoat Smartseal 30 D® from BASF. Another example is a copolymer comprising methyl methacrylate, butyl methacrylate and dimethylaminoethyl methacrylate such as commercially available as Eudragit E 100@ (granules) or Eudragit E PO® (powder) from Evonik. In certain embodiments, the polyacrylate is applied to the particles in an amount to provide a weight gain from about 10% (w/w) to about 90% (w/w); or from about 20% (w/w) to about 80% (w/w); or from about 30% (w/w) to about 70% (w/w); or from about 40% (w/w) to about 60% (w/w).

An example of a polysaccharide that can be utilized in the present invention is chitosan.

Examples of ion exchange resins that can be utilized in the present invention include polacrilex resin, polacrilin salt, sodium polystyrene sulfonate, cholestyramine resin or a mixture thereof.

In embodiments comprising a gelling agent in the matrix, the gelling agent may be in an amount from about 0.25% to about 50% (w/w) or from about 0.25% to about 10% (w/w) of the total dosage form.

The gelling agent utilized in the immediate release dosage forms of the present invention can be selected from sugars, sugar derived alcohols (e.g., mannitol, sorbitol, and the like), starch and starch derivatives, cellulose derivatives (e.g., microcrystalline cellulose, sodium carboxymethyl cellulose, methylcellulose, ethyl cellulose, hydroxyethyl cellulose, hydroxypropyl cellulose, and hydroxypropyl methylcellulose), attapulgites, bentonites, dextrins, alginates, carrageenan, gums (e.g., gum tragacanth, gum acacia, guar gum, and xanthan gum), pectin, gelatin, kaolin, lecithin, magnesium aluminum silicate, carbomers, carbopols, polyvinylpyrrolidone, polyethylene glycol, polyethylene oxide, polyvinyl alcohol, silicon dioxide, curdlan, furcelleran, egg white powder, lacto albumin, soy protein, chitosan, surfactants, mixed surfactant/wetting agent systems, emulsifiers, other polymeric materials, and mixtures thereof. In certain embodiments, the gelling agent is xanthan gum. In other embodiments, the gelling agent is pectin. The pectin or pectic substances include purified or isolated pectates and crude natural pectin from sources such as apple, citrus or sugar beet residues which have been subjected, when necessary, to esterification or de-esterification (e.g., by alkali or enzymes). The pectins may also be derived from citrus fruits such as lime, lemon, grapefruit, and orange. In particular embodiments, the gelling agent may be selected from the group consisting of pregelatinized starch (e.g., Swelstar® from Asahi Kasei), hydroxyethylcellulose (e.g., Natrosol® from Ashland Inc.), guar gum (e.g., Supercol® from Ashland Inc.), xanthan gum, alginate, carrageenan, polyethylene oxide and a mixture thereof.

The gelling agent is preferably included in the dosage form such that the viscosity of the dosage form mixed (crushed or intact) with from about 0.5 to about 10 ml of distilled water prevents or reduces the ability of the active agent (e.g., opioid agonist) from being drawn up into a syringe, or from being systemically absorbed when administered by the parenteral or nasal route. The viscosity can be, e.g., from about 10 cP to about 100 cP; from about 25 cP to about 75 cP; at least about 20 cP; at least about 40 cP or at least about 60 cP.

In certain embodiments, the weight amount of gelling agent contained in the immediate release dosage form of the present invention is not more than the weight amount of drug (e.g., opioid agonist). In other embodiments, the weight amount of gelling agent contained in the immediate release dosage forms of the present invention is less than the weight amount of drug. In further embodiments, the weight amount of gelling agent contained in the immediate release dosage forms of the present invention is more than the weight amount of drug.

In certain embodiments, the immediate release dosage forms of the present invention contain a weight ratio of gelling agent to drug (e.g., opioid agonist) from about 10:1 to about 1:10; from about 5:1 to about 1:5; from about 3:1 to about 1:3; from about 1:1 to about 1:1.5; from about 1.5:1 to about 1:1; about 1:1.25; or about 1.25:1.

In embodiments comprising a disintegrant in the matrix, the disintegrant may be in an amount from about 0.2% to about 25% (w/w) or from about 1% to about 10% (w/w) of the total dosage form.

The disintegrant can be selected from the group consisting of cross-linked sodium carboxymethylcellulose, starch, sodium starch glycolate, cross-linked polyvinylpyrrolidone, crospovidone and a mixture thereof.

In embodiments comprising a filler in the matrix, the filler may be a in an amount from about 15% to about 95% (w/w) or from about 25% to about 50% (w/w) of the total dosage form.

The filler can be a saccharide, e.g., selected from the group consisting of sucrose, dextrose, lactose, fructose, mannitol, a cellulosic derivative and a mixture thereof. In particular embodiments, the filler can be lactose (e.g., Fast Flo® from Foremost Farms) or microcrystalline cellulose (e.g., Avicel® from FMC BioPolymer.

In certain embodiments, the particles of the dosage form can be layered with a barrier layer. The barrier layer can be included, e.g., to provide stability or to prevent the migration of the active agent into the matrix. In embodiments with a barrier layer, the material and/or amount of material utilized preferably will not substantially interfere with the release profile of the active agent from the dosage form. The material for the barrier layer can be, e.g., an acrylic polymer, a cellulosic polymer or a vinyl polymer. Preferred barrier layers of the present invention include hydroxypropylmethylcellulose, polyvinyl alcohol, povidone or a mixture thereof. In certain embodiments, the barrier layer is applied to the particles in an amount to provide a weight gain from about 1% (w/w) to about 10% (w/w); or from about 4% (w/w) to about 7% (w/w).

The dosage forms of the present invention can include an aversive agent to further deter the illicit use of the active agent contained therein. The aversive agent can be included in the plurality of particles, the matrix, or in both components of the dosage form. The aversive agent can be, e.g., an emetic, an antagonist, a bittering agent, an irritant, or a mixture thereof.

The emetic may be selected from, e.g., the group consisting of methyl cephaeline, cephaeline, emetine hydrochloride, psychotrine, O-methylpsychotrine, emetamine, ipecamine, hydro-ipecamine, ipecacunhic acid and a mixture thereof. In particular embodiments, the emetic is ipecac.

The antagonist may be selected from, e.g., the group consisting of naltrexone, naloxone, nalmefene, cyclazacine, levallorphan, pharmaceutically acceptable salts thereof and mixtures thereof.

The bittering agent may be selected from, e.g., the group consisting of flavor oils, flavoring aromatics, oleoresins, plant extracts, leaf extracts, flower extracts, fruit extracts, sucrose derivatives, chlorosucrose derivatives, quinine sulphate, denatonium benzoate and a mixture thereof. In certain embodiments, the bittering agent is spearmint oil, peppermint oil, eucalyptus oil, oil of nutmeg, allspice, mace, oil of bitter almonds, menthol or a mixture thereof. In other embodiments, the bittering agent extracted from a fruit selected from the group consisting of lemon, orange, lime, grapefruit and a mixture thereof. In a particular embodiment, the bittering agent is denatonium benzoate.

The irritant may be selected from, e.g., a surfactant, capsaicin or a capsaicin analog. The capsaicin analog can be selected from the group consisting of resiniferatoxin, tinyatoxin, heptanoylisobutylamide, heptanoyl guaiacylamide, an isobutylamide, a guaiacylamide, dihydrocapsaicin, homovanillyl octylester, nonanoyl vanillylamide and a mixture thereof.

The surfactant can be selected from the group consisting of poloxamer, a sorbitan monoester, a glyceryl monooleate, sodium lauryl sulfate and a mixture thereof.

In certain embodiments, the immediate release solid oral dosage form of the present invention releases, e.g., at least about 70%, at least about 75%, at least about 80%, at least about 85%, at least about 90% or at least about 95% of the active agent (e.g., opioid agonist) within 45 minutes as measured by in-vitro dissolution in a USP Apparatus 2 (paddle) at 50 rpm in 500 ml 0.1N HCl or simulated gastric fluid without enzymes (SGF) at 37° C.

In certain embodiments, the immediate release solid oral dosage form of the present invention releases, e.g., at least about 85%, at least about 90%, at least about 95% or at least about 98% of the active agent (e.g., opioid agonist) within 60 minutes as measured by in-vitro dissolution in a USP Apparatus 2 (paddle) at 50 rpm in 500 ml 0.1N HCl or simulated gastric fluid without enzymes (SGF) at 37° C.

In certain embodiments, the immediate release solid oral dosage form of the present invention releases, e.g., at least about 70%, at least about 75%, at least about 80%, at least about 85%, at least about 90% or at least about 95% of the active agent (e.g., opioid agonist) within 45 minutes as measured by in-vitro dissolution in a USP Apparatus 1 (basket) at 50 rpm in 900 ml distilled water at 37° C.

In certain embodiments, the immediate release solid oral dosage form of the present invention releases, e.g., at least about 85%, at least about 90%, at least about 95% or at least about 98% of the active agent (e.g., opioid agonist) within 60 minutes as measured by in-vitro dissolution in a USP Apparatus 1 (basket) at 50 rpm in 900 ml distilled water at 37° C.

In certain embodiments, the immediate release solid oral dosage form of the present invention releases, e.g., one or more of (i) at least about 15%, at least about 25%, or at least about 35% of the active agent (e.g., opioid agonist) at 15 minutes or (ii) at least about 25%, at least about 35% or at least about 45% of the active agent at 30 minutes as measured by in-vitro dissolution in a USP Apparatus 2 (paddle) at 50 rpm in 500 ml distilled water at 37° C.

In certain embodiments, the immediate release solid oral dosage form of the present invention releases, e.g., (i) from about 15% to about 70% of the active agent (e.g., opioid agonist) at 15 minutes, (ii) from about 25% to about 80% of the active agent at 30 minutes, and at least about 90% of the active agent at 45 minutes as measured by in-vitro dissolution in a USP Apparatus 2 (paddle) at 50 rpm in 500 ml 0.1N HCl or simulated gastric fluid without enzymes (SGF) at 37° C.

In certain embodiments, the immediate release solid oral dosage form of the present invention releases, e.g., one or more of (i) at least about 15%, at least about 25%, or at least about 35% of the active agent (e.g., opioid agonist) at 15 minutes or (ii) at least about 25%, at least about 35% or at least about 45% of the active agent at 30 minutes as measured by in-vitro dissolution in a USP Apparatus 1 (basket) at 50 rpm in 900 ml distilled water at 37° C.

In certain embodiments, the immediate release solid oral dosage form of the present invention releases, e.g., (i) from about 15% to about 70% of the active agent (e.g., opioid agonist) at 15 minutes, (ii) from about 25% to about 80% of the active agent at 30 minutes, and at least about 90% of the active agent at 45 minutes as measured by in-vitro dissolution in a USP Apparatus 1 (basket) at 50 rpm in 900 ml distilled water at 37° C.

The immediate release dosage form of the present invention can be in the form of a compressed tablet or contained within a pharmaceutically acceptable capsule.

In a particular embodiment as depicted in FIG. 1, an immediate release dosage form (10) of the present invention may comprise a plurality of particles (11), each particle comprising (i) an active agent (12) (e.g., an opioid agonist); and (ii) a material that is sensitive to acidic pH (13) (e.g., chitosan, a polyacrylate or an ion exchange resin); wherein the plurality of particles are dispersed in a matrix (14) comprising (i) a gelling agent; (ii) a disintegrant; and (iii) a filler; wherein the dosage form releases at least about 85% of the active agent within 45 minutes as measured by in-vitro dissolution in a USP Apparatus 2 (paddle) at 50 rpm in 500 ml 0.1N HCl at 37° C.; and wherein the viscosity of the dosage form mixed with from about 0.5 to about 10 ml of distilled water which prevents or reduces the ability of the active agent from being drawn up into a syringe, or from being systemically absorbed, when administered by the parenteral or nasal route.

In certain embodiments, the recovery of the active agent (e.g., opioid agonist) is, e.g., less than about 10%, less than about 8%, less than about 6%, less than about 4%, less than about 2%, less than about 1%, less than about 0.8%, less than about 0.6%, less than about 0.4%, or less than less than about 0.2%, based on a syringability test whereby the dosage form is mixed or crushed and mixed with 5 mL solvent and the resultant solution is aspired with a 27½ gauge needle.

The solvent utilized in the syringability test can be, e.g., tap water, distilled water, sterile saline, vinegar or 40% ethanol. Also, during the syringability test, the solvent (before or after mixing with the dosage form) can be subject to heat from any source such as, e.g., by the use of a butane lighter.

In certain embodiments of the present invention, the recovery of the drug is, e.g., less than about 10%, less than about 8%, less than about 6%, less than about 4%, less than about 2%, less than about 1%, less than about 0.8%, less than about 0.6%, less than about 0.4%, or less than less than about 0.2%, based on both heated and unheated syringability tests, whereby the dosage form is mixed or crushed and mixed with 5 mL solvent and the resultant solution is aspired with a 27½ gauge needle.

In certain embodiments, the ratio of extraction from an unheated stability test to a heated stability test is from about 1:5 to about 5:1; from about 1:4 to about 4:1; from about 1:3 to about 3:1; from about 1:2 to about 2:1; from about 1:1.5 to about 1.5:1; from about 1:1.3 to about 1.3:1 or from about 1:1.1 to about 1.1:1.

Active Agents

In certain embodiments, the active agent used in the solid oral dosage form of the present invention is selected from the group consisting of ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, anti-pyretics, anti-inflammatory agents, androgens, local and general anesthetics, anti-addictive agents, anti-androgens, anti-arrhythmic agents, anti-asthmatic agents, anti-cholinergic agents, anti-cholinesterase agents, anti-coagulants, anti-diabetic agents, anti-diarrheal agents, anti-diuretic, anti-emetic agents, pro-kinetic agents, anti-epileptic agents, anti-estrogens, anti-fungal agents, anti-hypertensive agents, anti-microbial agents, anti-migraine agents, anti-muscarinic agents, anti-neoplastic agents, anti-parasitic agents, anti-parkinson's agents, anti-platelet agents, anti-progestins, anti-schizophrenia agents, anti-thyroid agents, anti-tussives, anti-viral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, cannabinoids, catecholamines and sympathomimetic drugs, cholinergic agonists, cholinesterase reactivators, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, 5-hydroxytryptamine antagonists, drugs for the treatment of hyperlipoproteinemia, hypnotics, sedatives, immunosuppressive agents, laxatives, methylxanthines, moncamine oxidase inhibitors, neuromuscular blocking agents, organic nitrates, opioid agonists, opioid antagonists, pancreatic enzymes, phenothiazines, progestins, prostaglandins, agents for the treatment of psychiatric disorders, psychotropics, retinoids, sodium channel blockers, agents for spasticity and acute muscle spasms, succinimides, testosterones, thioxanthines, thrombolytic agents, thyroid agents, tricyclic antidepressants, inhibitors of tubular transport of organic compounds, drugs affecting uterine motility, vasodilators, vitamins, and mixtures thereof.

In certain embodiments, the active agent is susceptible to abuse (e.g., an opioid analgesic such as an an opioid agonist). In such embodiments, the opioid analgesic is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. In certain embodiments, the opioid agonist is selected from the group consisting of codeine, fentanyl, hydromorphone, hydrocodone, oxycodone, dihydrocodeine, dihydromorphine, morphine, tramadol, oxymorphone, pharmaceutically acceptable salts thereof, and mixtures thereof.

In certain embodiments, the opioid agonist is oxycodone or pharmaceutically acceptable salts thereof in an amount, e.g., of about 2.5 mg, 5 mg, 7.5 mg, 10 mg, 15 mg, 20 mg, 25 mg or 30 mg.

In certain embodiments of the present invention, wherein the active agent is oxycodone hydrochloride, oxycodone hydrochloride is used having a 14-hydroxycodeinone level of less than about 25 ppm, less than about 15 ppm, less than about 10 ppm, less than about 5 ppm, less than about 2 ppm, less than about 1 ppm, less than about 0.5 ppm or less than about 0.25 ppm.

WO 2005/097801 A1, U.S. Pat. No. 7,129,248 B2 and US 2006/0173029 A1, all of which are hereby incorporated by reference, describe a process for preparing oxycodone hydrochloride having low levels of 14-hydroxycodeinone.

In certain embodiments, the oral solid dosage form of the present invention comprises an active agent that is an opioid antagonist (with or without an opioid agonist). In such embodiments, the opioid antagonist is selected from the group consisting of amiphenazole, naltrexone, methylnaltrexone, naloxone, nalbuphine, nalorphine, nalorphine dinicotinate, nalmefene, nadide, levallorphan, cyclozocine, pharmaceutically acceptable salts thereof and mixtures thereof.

In certain embodiments, the solid oral dosage form of the present invention comprises an active agent that is a non-opioid analgesic. In such embodiments, the non-opioid analgesic is acetaminophen or a non-steroidal anti-inflammatory agent selected from the group consisting of aspirin, celecoxib, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof and mixtures thereof.

In other embodiments, the present invention is directed to the dosage forms disclosed herein utilizing active agents such as benzodiazepines, barbiturates or amphetamines, their antagonists, or combinations thereof.

Benzodiazepines to be used in the present invention may be selected from alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, and pharmaceutically acceptable salts, hydrates, and solvates and mixtures thereof. Benzodiazepine antagonists that can be used in the present invention include, but are not limited to, flumazenil and pharmaceutically acceptable salts, hydrates, and solvates.

Barbiturates to be used in the present invention include, but are not limited to, amobarbital, aprobarbotal, butabarbital, butalbital, methohexital, mephobarbital, metharbital, pentobarbital, phenobarbital, secobarbital and pharmaceutically acceptable salts, hydrates, and solvates mixtures thereof. Barbiturate antagonists that can be used in the present invention include, but are not limited to, amphetamines and pharmaceutically acceptable salts, hydrates, and solvates.

Stimulants to be used in the present invention include, but are not limited to, amphetamines, such as amphetamine, dextroamphetamine resin complex, dextroamphetamine, methamphetamine, methylphenidate and pharmaceutically acceptable salts, hydrates, and solvates and mixtures thereof. Stimulant antagonists that can be used in the present invention include, but are not limited to, benzodiazepines, and pharmaceutically acceptable salts, hydrates, and solvates as described herein.

In embodiments comprising a first active agent and a second active agent as disclosed herein (e.g., the first active agent is a substrate for coating a second active agent thereon), the first active agent can be a non-opioid analgesic and the second active agent can be an opioid agonist. Alternatively, the first active agent can be an opioid agonist and the second active agent can be a non-opioid analgesic. In particular embodiments, the non-opioid analgesic is acetaminophen or a non-steroidal anti-inflammatory agent (e.g., ibuprofen, aspirin or diclofenac) and the opioid agonist is oxycodone, hydrocodone or pharmaceutically acceptable salts thereof (e.g., oxycodone hydrochloride or hydrocodone bitartrate).

The immediate release solid oral dosage forms of the present invention may comprise, e.g., from about 2.5 mg to about 10 mg oxycodone or a pharmaceutically acceptable salt thereof; from about 2.5 mg to about 15 mg hydrocodone or a pharmaceutically acceptable salt thereof; from about 325 mg to about 650 mg acetaminophen; from about 100 mg to about 800 mg ibuprofen, or from about 325 mg to about 750 mg aspirin.

Specific formulations may comprise about 2.5 mg oxycodone or a pharmaceutically acceptable salt thereof and about 325 mg acetaminophen; about 5 mg oxycodone or a pharmaceutically acceptable salt thereof and about 325 mg acetaminophen; about 7.5 mg oxycodone or a pharmaceutically acceptable salt thereof and about 325 mg acetaminophen; about 10 mg oxycodone or a pharmaceutically acceptable salt thereof and about 325 mg acetaminophen; about 7.5 mg oxycodone or a pharmaceutically acceptable salt thereof and about 500 mg acetaminophen; about 10 mg oxycodone or a pharmaceutically acceptable salt thereof and about 650 mg acetaminophen; about 5 mg oxycodone or a pharmaceutically acceptable salt thereof and about 500 mg acetaminophen; about 2.5 mg oxycodone or a pharmaceutically acceptable salt thereof and about 300 mg acetaminophen; about 5 mg oxycodone or a pharmaceutically acceptable salt thereof and about 300 mg acetaminophen; about 7.5 mg oxycodone or a pharmaceutically acceptable salt thereof and about 300 mg acetaminophen; about 10 mg oxycodone or a pharmaceutically acceptable salt thereof and about 400 mg acetaminophen; about 2.5 mg oxycodone or a pharmaceutically acceptable salt thereof and about 400 mg acetaminophen; about 5 mg oxycodone or a pharmaceutically acceptable salt thereof and about 400 mg acetaminophen; or about 7.5 mg oxycodone or a pharmaceutically acceptable salt thereof and about 400 mg acetaminophen.

Other formulations may comprise about 2.5 mg oxycodone or a pharmaceutically acceptable salt thereof and about 325 mg aspirin; about 5 mg oxycodone or a pharmaceutically acceptable salt thereof and about 325 mg aspirin; about 7.5 mg oxycodone or a pharmaceutically acceptable salt thereof and about 325 mg aspirin; about 10 mg oxycodone or a pharmaceutically acceptable salt thereof and about 325 mg aspirin; about 2.5 mg oxycodone or a pharmaceutically acceptable salt thereof and about 500 mg aspirin; about 5 mg oxycodone or a pharmaceutically acceptable salt thereof and about 500 mg aspirin; about 7.5 mg oxycodone or a pharmaceutically acceptable salt thereof and about 500 mg aspirin; about 10 mg oxycodone or a pharmaceutically acceptable salt thereof and about 500 mg aspirin In certain embodiments, the formulation comprises about 4.8355 mg oxycodone or a pharmaceutically acceptable salt thereof and 325 mg aspirin.

Further formulations may comprise about 5 mg hydrocodone or a pharmaceutically acceptable salt thereof and about 500 mg acetaminophen; about 10 mg hydrocodone or a pharmaceutically acceptable salt thereof and about 660 mg acetaminophen; about 7.5 mg hydrocodone or a pharmaceutically acceptable salt thereof and about 750 mg acetaminophen; about 5 mg hydrocodone or a pharmaceutically acceptable salt thereof and about 325 mg acetaminophen; about 7.5 mg hydrocodone or a pharmaceutically acceptable salt thereof and about 325 mg acetaminophen; about 10 mg hydrocodone or a pharmaceutically acceptable salt thereof and about 325 mg acetaminophen; about 7.5 mg hydrocodone or a pharmaceutically acceptable salt thereof and about 650 mg acetaminophen; about 10 mg hydrocodone or a pharmaceutically acceptable salt thereof and about 750 mg acetaminophen; about 10 mg hydrocodone or a pharmaceutically acceptable salt thereof and about 500 mg acetaminophen; about 5 mg hydrocodone or a pharmaceutically acceptable salt thereof and about 400 mg acetaminophen; about 7.5 mg hydrocodone or a pharmaceutically acceptable salt thereof and about 400 mg acetaminophen; about 10 mg hydrocodone or a pharmaceutically acceptable salt thereof and about 400 mg acetaminophen.

Additional formulations may comprise about 2.5 mg hydrocodone or a pharmaceutically acceptable salt thereof and about 200 mg ibuprofen; about 5 mg hydrocodone or a pharmaceutically acceptable salt thereof and about 200 mg ibuprofen; about 7.5 mg hydrocodone or a pharmaceutically acceptable salt thereof and about 200 mg ibuprofen; or about 10 mg hydrocodone or a pharmaceutically acceptable salt thereof and about 200 mg ibuprofen.

Pharmacokinetic Parameters

In preferred embodiments, the formulations of the present invention comprise an opioid agonist (e.g., oxycodone hydrochloride) and preferably provide a Tmax from about 0.5 hour to about 6 hours, or from about 1 hour to about 5 hours, or from about 2 hours to about 4 hours, or from about 2 hours to about 3 hours, or from about 1 hour to about 3 hours, or about 2.5 hours.

In embodiments comprising oxycodone or a pharmaceutically acceptable salt thereof (e.g., oxycodone hydrochloride), the formulation preferably provides a Cmax of about 30 ng/mL to about 50 ng/mL, or about 35 ng/mL to about 45 ng/mL, or about 38 to about 42 ng/mL based on a single dose of about 15 mg to a subject; or a mean Cmax of about 30 ng/mL to about 50 ng/mL, or about 35 ng/mL to about 45 ng/mL, or about 38 to about 38 ng/mL based on a single dose of about 15 mg to a population of subjects.

In embodiments comprising oxycodone or a pharmaceutically acceptable salt thereof (e.g., oxycodone hydrochloride), the formulation preferably provides a Cmax of about 20 ng/mL to about 35 ng/mL, or about 22 ng/mL to about 32 ng/mL, or about 25 to about 30 ng/mL based on a single dose of about 10 mg to a subject; or a mean Cmax of about 20 ng/mL to about 35 ng/mL, or about 22 ng/mL to about 32 ng/mL, or about 25 to about 30 ng/mL based on a single dose of about 10 mg to a population of subjects.

In embodiments comprising oxycodone or a pharmaceutically acceptable salt thereof (e.g., oxycodone hydrochloride), the formulation preferably provides a Cmax of about 8 ng/mL to about 20 ng/mL, or about 10 ng/mL to about 18 ng/mL, or about 12 to about 16 ng/mL based on a single dose of about 5 mg to a subject; or a mean Cmax of about 8 ng/mL to about 20 ng/mL, or about 10 ng/mL to about 18 ng/mL, or about 12 to about 16 ng/mL based on a single dose of about 5 mg to a population of subjects.

In embodiments comprising oxycodone or a pharmaceutically acceptable salt thereof (e.g., oxycodone hydrochloride), the formulation preferably provides a Cmax of about 4 ng/mL to about 12 ng/mL, or about 5 ng/mL to about 10 ng/mL, or about 6 to about 8 ng/mL based on a single dose of about 2.5 mg to a subject; or a mean Cmax of about 4 ng/mL to about 12 ng/mL, or about 5 ng/mL to about 10 ng/mL, or about 6 to about 8 ng/mL based on a single dose of about 2.5 mg to a population of subjects.

In embodiments comprising oxycodone or a pharmaceutically acceptable salt thereof (e.g., oxycodone hydrochloride), the formulation preferably provides a $AUC_{o-t}$ of about 150 ng*h/mL to about 350 ng*h/mL, or about 200 ng*h/mL to about 300 ng*h/mL, or about 225 ng*h/mL to about 275 ng*h/mL based on a single dose of about 15 mg to a subject; or a mean $AUC_{o-t}$ of about 150 ng*h/mL to about 350 ng*h/mL, or about 200 ng*h/mL to about 300 ng*h/mL, or about 225 ng*h/mL to about 275 ng*h/mL based on a single dose of about 15 mg to a population of subjects.

In embodiments comprising oxycodone or a pharmaceutically acceptable salt thereof (e.g., oxycodone hydrochloride), the formulation preferably provides a $AUC_{o-t}$ of about 100 ng*h/mL to about 300 ng*h/mL, or about 120 ng*h/mL to about 240 ng*h/mL, or about 150 ng*h/mL to about 200 ng*h/mL based on a single dose of about 10 mg to a subject; or a mean $AUC_{o-t}$ of about 100 ng*h/mL to about 300 ng*h/mL, or about 120 ng*h/mL to about 240 ng*h/mL, or about 150 ng*h/mL to about 200 ng*h/mL based on a single dose of about 10 mg to a population of subjects.

In embodiments comprising oxycodone or a pharmaceutically acceptable salt thereof (e.g., oxycodone hydrochloride), the formulation preferably provides a $AUC_{o-t}$ of about 50 ng*h/mL to about 150 ng*h/mL, or about 60 ng*h/mL to about 120 ng*h/mL, or about 75 ng*h/mL to about 100 ng*h/mL based on a single dose of about 5 mg to a subject; or a mean $AUC_{o-t}$ of about 50 ng*h/mL to about 150 ng*h/mL, or about 60 ng*h/mL to about 120 ng*h/mL, or about 75 ng*h/mL to about 100 ng*h/mL based on a single dose of about 5 mg to a population of subjects.

In embodiments comprising oxycodone or a pharmaceutically acceptable salt thereof (e.g., oxycodone hydrochloride), the formulation preferably provides a $AUC_{o-t}$ of about 20 ng*h/mL to about 100 ng*h/mL, or about 25 ng*h/mL to about 75 ng*h/mL, or about 30 ng*h/mL to about 50 ng*h/mL based on a single dose of about 2.5 mg to a subject; or a mean $AUC_{o-t}$ of about 20 ng*h/mL to about 100 ng*h/mL, or about 25 ng*h/mL to about 75 ng*h/mL, or about 30 ng*h/mL to about 50 ng*h/mL based on a single dose of about 2.5 mg to a population of subjects.

Methods of Manufacture

The present invention is also directed to a process for preparing the immediate release solid oral dosage forms disclosed herein. In certain embodiments, the process comprises (i) preparing a plurality of particles, each particle comprising an active agent and a material that is sensitive to acidic pH; and (ii) dispersing the plurality of particles into a matrix; wherein the dosage form releases at least about 85% of the active agent within 45 minutes as measured by in-vitro dissolution in a USP Apparatus 2 (paddle) at 50 rpm in 500 ml 0.1N HCl at 37° C.

In another embodiment, the process comprises dispersing a plurality of particles, each particle comprising an active agent and a material that is sensitive to acidic pH, into a matrix; wherein the dosage form releases at least about 85% of the active agent within 45 minutes as measured by in-vitro dissolution in a USP Apparatus 1 (paddle) at 50 rpm in 500 ml 0.1N HCl at 37° C.

In certain embodiments, the matrix can include one or more of a gelling agent, a disintegrant or a filler.

The particles can be prepared by layering a core comprising the active agent with the material that is sensitive to acidic pH. The core can be prepared by layering an inert excipient (e.g., a microcrystalline cellulose bead or a sugar sphere) with an active agent or by dispersing the active agent in a pharmaceutically acceptable excipient. Alternatively, an active agent (e.g., acetaminophen) can be used in place of the inert excipient with an additional active agent (e.g., an opioid agonist) layered thereon.

In other embodiments, the particles can be prepared by layering a core comprising an inert excipient with a coating comprising the active agent and the material that is sensitive to acidic pH. In alternative embodiments, the particles can be prepared by dispersing the active agent in the material that is sensitive to acidic pH.

In alternative embodiments, the immediate release dosage forms of the present invention can be prepared by (i) granulating an active agent and a material that is sensitive to acidic pH to obtain a granulation; (ii) compressing the granulation into a tablet or containing the granulation in a capsule; wherein the dosage form releases at least about 85% of the active agent within 45 minutes as measured by in-vitro dissolution in a USP Apparatus 1 (paddle) at 50 rpm in 500 ml 0.1N HCl at 37° C.

Figure 2:
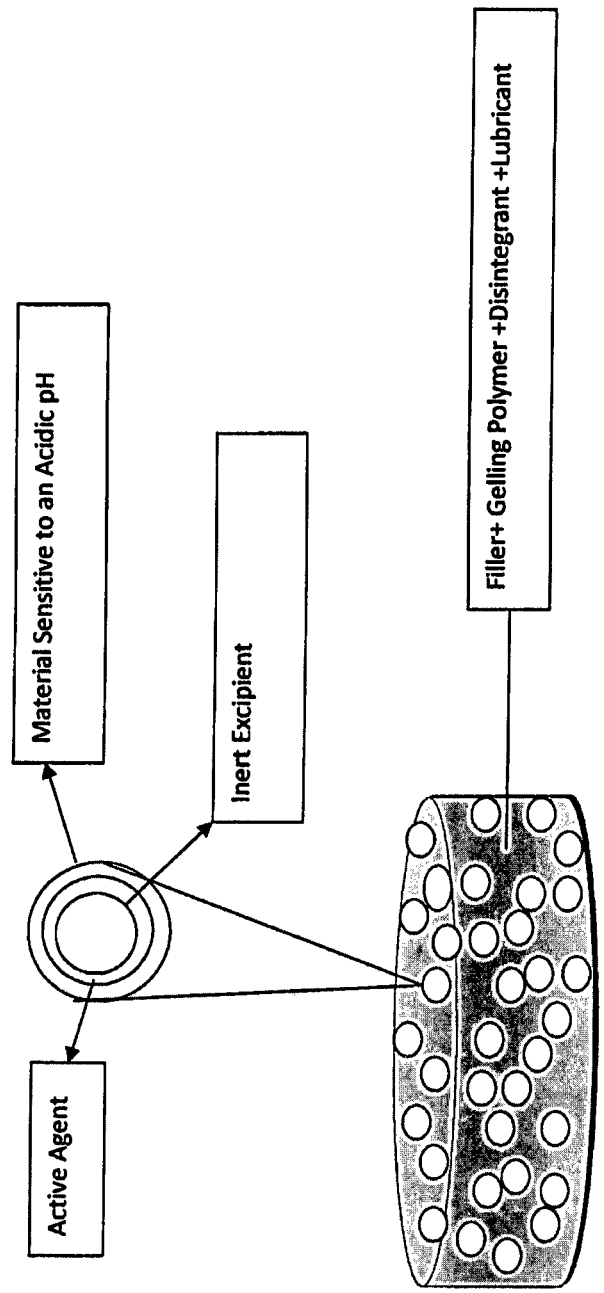
FIG. 2 is an alternate graphical depiction of a formulation according to the present invention.
Figure 3:
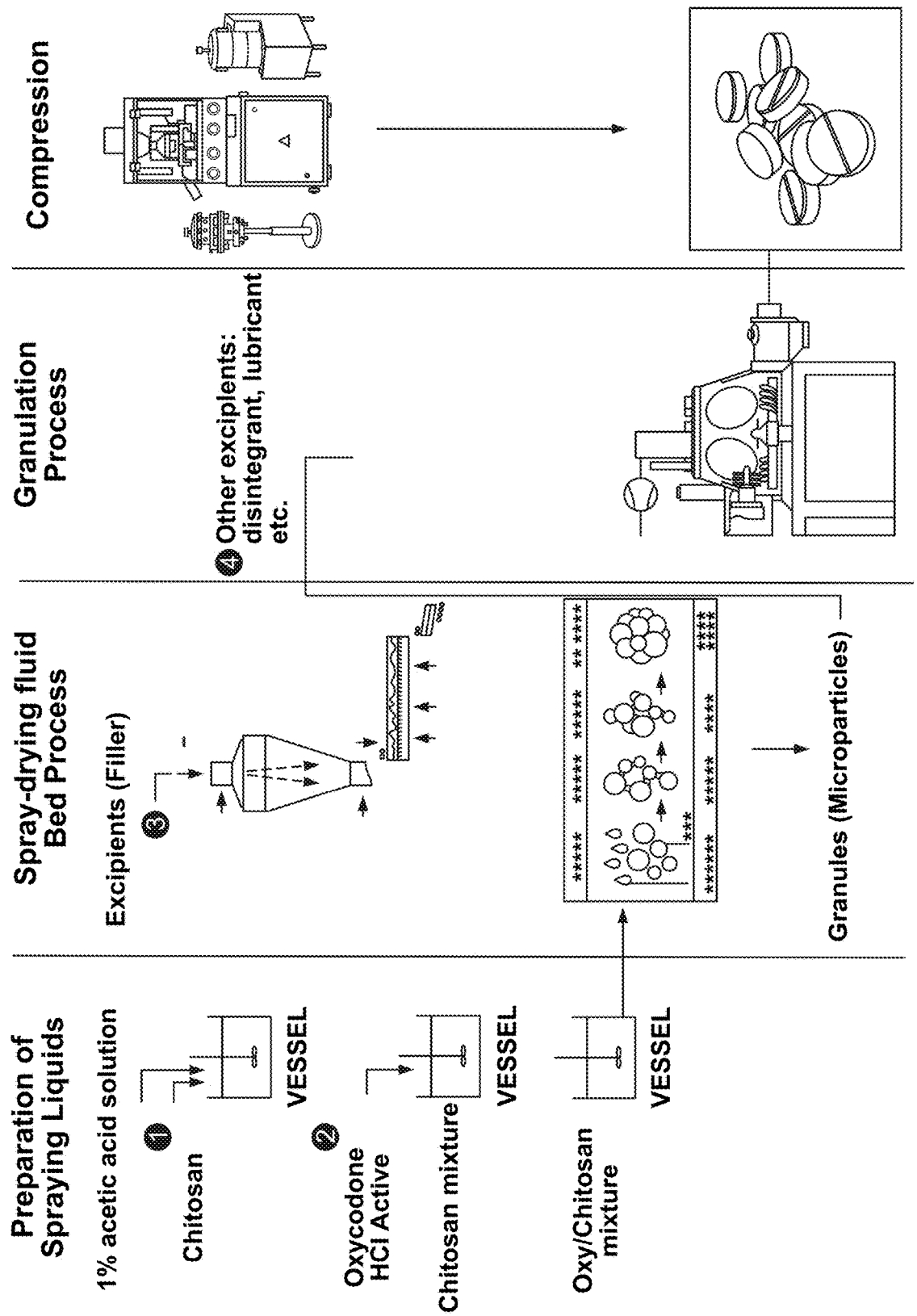
FIG. 3 is a graphical depiction of a process for preparing an embodiment of the present invention.

This process may also incorporate one or more of a gelling agent, a disintegrant or a filler. The filler can be spray dried with a solution comprising the active agent and the acid pH sensitive material to obtain a spray dried composition as depicted in FIGS. 2 and 3. The spray dried granulation may then be granulated with the gelling agent and the disintegrant and other excipients prior to compression into a unit dosage form as further depicted in FIGS. 2 and 3.

Methods of Treatment

The present invention is further directed to a method of treating a disease or condition comprising administering any of the immediate release solid oral dosage forms described herein to a patient in need thereof. In certain embodiments, the patient is treated for pain, diarrhea, or constipation.

Types of pain that can be treated with the immediate release solid oral dosage forms of the present invention include pain caused by pancreatitis, kidney stones, headaches, dysmenorrhoea, musculoskeletal pain, sprains, visceral pain, ovarian cysts, prostatitis, cystitis, interstitial cystitis, inflammatory bowel disease, post-operative pain, dental pain, post-surgical pain, migraine, trigeminal neuralgia, pain from burns and/or wounds, pain associated with trauma, neuropathic pain, post-herpetic neuralgia, pain associated with musculoskeletal diseases, rheumatoid arthritis, osteoarthritis, ankylosing spondylitis, periarticular pathologies, oncological pain, pain from bone metastase, pain from HIV or pain from myocardial infarction. In certain embodiments, the immediate release solid oral dosage forms of the present invention can be used to treat "break through" pain (i.e., pain that comes on suddenly for short periods of time and is not alleviated by the patients' normal pain management).

The method of treatment of the present invention may comprise administering the solid oral dosage form described herein in combination with another pharmaceutical composition. In certain embodiments, the other pharmaceutical composition is administered to treat the same condition or disease. In other embodiments, the other pharmaceutical composition is administered to treat a different condition or disease.

In certain embodiments, the method of treatment of the present invention further comprises monitoring the patient for how the patient metabolizes the active agent, or how the patient responds to the active agent. In certain embodiments, the method of treatment further comprises altering the dose of the solid oral dosage form in response to said monitoring. In certain embodiments, certain baseline measurements are taken from the patient prior to administering the oral solid dosage form to the patient.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Examples

Example 1

Formulations 1 A to 1O are gelling matrices that can be utilized in the present invention for dispersing active agent particles comprising a material sensitive to acidic pH. The formulations were prepared in accordance with the following general procedure (the procedures can be modified to use particles of the present invention in place of naloxone):

Procedure:
1. Pass items #1-5 (naloxone, lactose, microcrystalline cellulose (MCC), gelling polymer and crospovidone, respectively) through a 20 Mesh screen and load into a V-blender and mix for 10 minutes.
2. Pass item #6 (magnesium stearate) through a 30 Mesh screen into the above V-blender and mix for 3 minutes.
3. Compress the mixture of step 2 above into tablets (round shape) at a target weight of 500 mg and a target hardness of 3-5 kp using a Stokes, Fette or Killian rotary press.

Tables 1A to 1O show the formulations of Examples 1A and 1O, respectively.

TABLE 1A

| No. | Ingredients | mg/tab | Qty/Batch (g) | % |
|---|---|---|---|---|
| 1 | HCl Dihydrate | 6.10 | 1.83 | 1.220 |
| 2 | Lactose Monohydrate (Fast Flo 316) | 232.58 | 69.77 | 46.515 |
| 3 | MCC (Avicel pH 102) | 232.58 | 69.77 | 46.515 |
| 4 | N/A | 0.00 | 0.00 | 0.000 |
| 5 | Crospovidone | 25.00 | 7.50 | 5.000 |
| 6 | Magnesium Stearate | 3.75 | 1.13 | 0.750 |
| | Total | 500 | 150 | 100.0 |

TABLE 1B

| No. | Ingredients | mg/tab | Qty /Batch (g) | % |
|---|---|---|---|---|
| 1 | Naloxone HCl Dihydrate | 6.10 | 1.83 | 1.220 |
| 2 | Lactose Monohydrate (Fast Flo 316) | 230.08 | 69.02 | 46.015 |
| 3 | MCC (Avicel pH 102) | 230.08 | 69.02 | 46.015 |
| 4 | Hydroxyethylcellulose (Natrosol-HHX) | 5.00 | 1.50 | 1.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1C

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 220.08 | 66.02 | 44.015 |
| 3 | MCC (Avicel pH 102) | 220.08 | 66.02 | 44.015 |
| 4 | Hydroxyethylcellulose (Natrosol-HHX) | 25.00 | 7.50 | 5.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1D

| No. | Ingredients | mg/tab | Qty /Batch (g) | % |
|---|---|---|---|---|
| 1 | Naloxone HCl Dihydrate | 6.10 | 1.83 | 1.220 |
| 2 | Lactose Monohydrate (Fast Flo 316) | 215.08 | 64.52 | 43.015 |
| 3 | MCC (Avicel pH 102) | 215.08 | 64.52 | 43.015 |
| 4 | Hydroxyethylcellulose (Natrosol-HHX) | 35.00 | 10.50 | 7.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1E

| No. | Ingredients | mg/tab | Qty/Batch (gram) | % |
|---|---|---|---|---|
| 1 | Naloxone HCl Dihydrate | 6.10 | 1.83 | 1.220 |
| 2 | Lactose Monohydrate (Fast Flo 316) | 207.58 | 62.27 | 41.515 |
| 3 | MCC (Avicel pH 102) | 207.58 | 62.27 | 41.515 |
| 4 | Hydroxyethylcellulose (Natrosol-HHX) | 50.00 | 15.00 | 10.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1F

| No. | Ingredients | mg/tab | Qty /Batch(g) | % |
|---|---|---|---|---|
| 1 | Naloxone HCl Dihydrate | 6.10 | 1.83 | 1.220 |
| 2 | Lactose Monohydrate (Fast Flo 316) | 182.58 | 54.77 | 36.515 |
| 3 | MCC (Avicel pH 102) | 182.58 | 54.77 | 36.515 |
| 4 | Hydroxyethylcellulose (Natrosol-HHX) | 100.00 | 30.00 | 20.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1G

| No. | Ingredients | mg/tab | Qty/Batch (gram) | % |
|---|---|---|---|---|
| 1 | Naloxone HCl Dihydrate | 6.10 | 1.83 | 1.220 |
| 2 | Lactose Monohydrate (Fast Flo 316) | 226.33 | 67.90 | 45.265 |
| 3 | MCC (Avicel pH 102) | 226.33 | 67.90 | 45.265 |
| 4 | Guar Gum (Supercol U) | 12.50 | 3.75 | 2.500 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1H

| No. | Ingredients | mg/tab | Qty/Batch (gram) | % |
|---|---|---|---|---|
| 1 | Naloxone HCl Dihydrate | 6.10 | 1.83 | 1.220 |
| 2 | Lactose Monohydrate (Fast Flo 316) | 220.08 | 66.02 | 44.015 |
| 3 | MCC (Avicel pH 102) | 220.08 | 66.02 | 44.015 |
| 4 | Guar Gum (Supercol U) | 25.00 | 7.50 | 5.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1I

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 207.58 | 62.27 | 41.515 |
| 3 | MCC (Avicel pH 102) | 207.58 | 62.27 | 41.515 |
| 4 | Guar Gum (Supercol U) | 50.00 | 15.00 | 10.000 |
| 5 | Crospoyidone | 25.00 | 7.50 | 5.000 |
| 6 | Magnesium Stearate | 3.75 | 1.13 | 0.750 |
|   | Total | 500 | 150 | 100.0 |

TABLE 1J

| No. | Ingredients | mg/tab | Qty/Batch (gram) | % |
|---|---|---|---|---|
| 1 | Naloxone HCl Dihydrate | 6.10 | 1.83 | 1.220 |
| 2 | Lactose Monohydrate (Fast Flo 316) | 220.08 | 66.02 | 44.015 |
| 3 | MCC (Avicel pH 102) | 220.08 | 66.02 | 44.015 |
| 4 | Hydroxyethylcellulose (Natrosol-HX) | 25.00 | 7.50 | 5.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1K

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 207.58 | 62.27 | 41.515 |
| 3 | MCC (Avicel pH 102) | 207.58 | 62.27 | 41.515 |
| 4 | Hydroxyethylcellulose (Natrosol-HX) | 50.00 | 15.00 | 10.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1L

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 182.58 | 54.77 | 36.515 |
| 3 | MCC (Avicel pH 102) | 182.58 | 54.77 | 36.515 |
| 4 | Hydroxyethylcellulose (Natrosol-HX) | 100.00 | 30.00 | 20.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1M

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 230.08 | 69.02 | 46.015 |
| 3 | MCC (Avicel pH 102) | 230.08 | 69.02 | 46.015 |
| 4 | Pregelatinized Starch (Swelstar MX-1) | 5.00 | 1.50 | 1.000 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1N

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 226.33 | 67.90 | 45.265 |
| 3 | MCC (Avicel pH 102) | 226.33 | 67.90 | 45.265 |
| 4 | Pregelatinized Starch (Swelstar MX-1) | 12.50 | 3.75 | 2.500 |
| 5 | Crospovidone | 25.00 | 7.50 | 5.000 |
| 6 | Magnesium Stearate | 3.75 | 1.13 | 0.750 |
|   | Total | 500 | 150 | 100.0 |

TABLE 1O

| No. | Ingredients | mg/tab | Qty/Batch (g) | % |
|---|---|---|---|---|
| 1 | Naloxone HCl Dihydrate | 6.10 | 1.83 | 1.220 |
| 2 | Lactose Monohydrate (Fast Flo 316) | 220.08 | 66.02 | 44.015 |
| 3 | MCC (Avicel pH 102) | 220.08 | 66.02 | 44.015 |
| 4 | Pregelatinized Starch (Swelstar MX-1) | 25.00 | 7.50 | 5.000 |
| 5 | Crospovidone | 25.00 | 7.50 | 5.000 |
| 6 | Magnesium Stearate | 3.75 | 1.13 | 0.750 |
| | Total | 500 | 150 | 100.0 |

Example 2

Formulations 2A (Pellets) and 2B (Tablets) were prepared in accordance with the following general procedure:

Procedure for 2A & 2B:

1. Add item #2 (naloxone) and item #5 (talc) to item #6 (water) and mix for approximately 30 minutes in a mixing vessel, such as a V-blender.
2. While still stirring, add item #3 (aqueous dispersion of a co-polymer comprising methyl methacrylate and diethylaminoethyl methacrylate (Kollicoat Smartseal 30 D)) and item #4 (triethyl citrate) into the above drug suspension, keep mixing for at least 2 hours. Homogenize for 5 minutes and screen through 200 Mesh screen before spraying.
3. Load item #1 (microcrystalline cellulose spheres) in a spray dryer (GPCG-3 fluid bed dryer). Set up the machine and spray step #2 coating suspension at about 5-15 g/minutes.
4. After completing the spray process, continue to dry the resultant beads or pellets for approximately 30 minutes at about 40±5° C.
5. Collect the coated beads of Example 2A after passing through 40 Mesh and 100 Mesh screens consecutively to remove lumps and fines.
6. Mix the coated beads with other excipients in Example 2B (lactose, microcrystalline cellulose, gelling polymer, crospovidone, and magnesium stearate and compress into tablets at a target weight of 500 mg and target hardness of 3-5 kP using a Stokes, Fette or Killian rotary press.

Tables 2A and 2B show the formulations of Examples 2A and 2B, respectively.

TABLE 2A

| | Ingredient | Liquid (g) | Solid (g) |
|---|---|---|---|
| 1 | MCC Sphere | | 1500 |
| 2 | Naloxone HCl Dihydrate | | 52 |
| 3 | Kollicoat Smartseal 30 D | 1000 | 300 |
| 4 | Triethyl Citrate | 45 | 45 |
| 5 | Talc | | 240 |
| 6 | Water | 1663 | |
| | Total solution | 3000 | |
| | Total solids: | | 2137 |

TABLE 2B

| No. | Ingredients | mg/tab | % |
|---|---|---|---|
| 1 | Drug Layered MCC Pellets of Ex. 2A | 250.00 | 50.000 |
| 2 | Lactose Monohydrate (Fast Flo 316) | 216.00 | 43.200 |
| 3 | Avicel pH 102 | 0.00 | 0.000 |
| 4 | Pregelatinized Starch (Swelstar MX-1) | 5.00 | 1.000 |
| 5 | Crospovidone | 25.00 | 5.000 |
| 6 | Magnesium stearate | 3.75 | 0.750 |
| | Total | 500 | 100.0 |

Dissolution was tested on Example 2B under the following conditions:

Method: USP apparatus II (Paddle)
Paddle speed: 75 rpm
Medium: Distilled water or 0.1N HCl
Volume: 500 mL
Sampling intervals: 5, 10, 15, 30, 45 and 60 minutes Table 2C shows the dissolution data of Example 2B in both water and 0.1N HCl.

TABLE 2C

| Time | Dissolution of Naloxone in Media (% Dissolved) (n = 3) | |
|---|---|---|
| (Minutes) | Water | 0.1N HCl |
| 0 | 0 | 0 |
| 5 | 86 | 54 |
| 10 | 91 | 91 |
| 15 | 95 | 100 |
| 30 | 98 | 101 |
| 45 | 100 | 102 |
| 60 | 101 | 110 |

Example 3

Formulations 3A (Pellets) and 3B (Tablets) were prepared in accordance with the following general procedure:

Procedure for 3A & 3B:

1. Add item #5 (talc) to item #6 (water) and mix for approximately 30 minutes in a mixing vessel, such as a V-blender.
2. While stirring, add item #3 (aqueous dispersion of a co-polymer comprising methyl methacrylate and diethylaminoethyl methacrylate) and item #4 (triethyl citrate) to the above suspension. Continue to mix for at least 2 hours.
3. Divide the above coating suspension into two parts (500 ml Part I, and 2500 ml Part II). Add item #2 (naloxone) to Part I and keep mixing.
4. Homogenize both Parts I and II coating suspensions for approximately 5 minutes and screen through 200 Mesh before spraying.
5. Load item #1 (microcrystalline cellulose spheres) in a spray dryer (GPCG-3 fluid bed dryer) and set up the machine with appropriate process parameters. Spray step 4 coating suspension at approximately 5-15 g/minutes, beginning first with Part I, and then with Part II.
6. After completing the spray process, continue to dry the pellets for approximately 30 minutes at approximately 40±5° C.
7. Collect the coated beads of Example 3A after respectively screening through 40 Mesh and 100 Mesh sieves to remove lumps and fines.
8. Mix the coated beads with other excipients in Example #3B (lactose, microcrystalline cellulose, gelling polymer, crospovidone and magnesium stearate) and compress to make tablets at a target weight of 500 mg and a target hardness of approximately 3-5 kp using a Stokes, Fette or Killian rotary press.

Tables 3A and 3B show the formulations of Examples 3A and 3B, respectively.

TABLE 3A

|   | Ingredient | Liquid (g) | Solid (g) |
|---|---|---|---|
| 1 | MCC Sphere | | 1000.0 |
| 2 | Naloxone HCl Dihydrate | | 35.0 |
| 3 | Kollicoat Smartseal 30 D | 1000 | 300 |
| 4 | Triethyl Citrate | 45 | 45 |
| 5 | Talc | | 240 |
| 6 | Water | 1680 | |
| | Total solution | 3000 | |
| | | Total solids: | 1620 |

TABLE 3B

| No. | Ingredients | mg/tab | % | Lot # |
|---|---|---|---|---|
| 1 | Drug Layered MCC Pellets of Ex. 3A | 330.00 | 66.000 | Example 3A |
| 2 | Lactose Monohydrate (Fast Flo 316) | 136.00 | 27.200 | 8511071661 |
| 3 | Avicel pH 102 | 0.00 | 0.000 | P211823096 |
| 4 | Pregelatinized Starch(Swelstar MX-1) | 5.00 | 1.000 | 9111 |
| 5 | Crospovidone | 25.00 | 5.000 | 54752224U0 |
| 6 | Magnesium stearate | 3.75 | 0.750 | CO05160 |
| | Total | 500 | 100.0 | |

Dissolution testing was performed on Example 3B under the following conditions:
Method: USP apparatus II (Paddle)
Paddle speed: 75 rpm
Medium: Distilled water or 0.1N HCl
Volume: 500 mL
Sampling intervals: 5, 10, 15, 30, 45 and 60 minutes Table 3C shows the dissolution data of Example 3B in both water and 0.1N HCl.

TABLE 3C

| Time | Dissolution of Naloxone in different media (% Dissolved) (n = 3) | |
|---|---|---|
| (Minutes) | Water | 0.1N HCl |
| 0 | 0 | 0 |
| 5 | 6 | 31 |
| 10 | 15 | 52 |
| 15 | 21 | 62 |
| 30 | 36 | 82 |
| 45 | 50 | 92 |
| 60 | 62 | 98 |

Example 4

Formulation 4 A (Drug Layered Pellet), 4B (Acrylic Coated Pellets with Kollicoat Smartseal 30D), 4C (Acrylic Coated Pellets with Eudragit E100), 4D (Tablets) and 4E (Tablets) were prepared in accordance with the following general procedure:

Procedure for 4 A, 4B, 4C, 4D & 4E:
4 A: Drug layer coating
  Dissolve item #3 (povidone) into item #4 (water) to make a binder solution, and add item #2 (naloxone) into the binder to prepare a coating solution. Spray the above coating solution onto item #1 (MCC spheres) using a GPCG-3. Use the drug layered pellets for the following examples 4B and 4C for further coating.

4B & 4D: Kollicoat Smartseal 30D top layered pellets and tablets
1. Add item #4 (talc) to item #5 (water) and mix for approximately 30 minutes.
2. While stirring, add items #2 (Kollicoat Smartseal 30D) and #3 (Triethyl Citrate) to the above suspension and continue mixing for at least 2 hours.
3. Homogenize the above coating suspension for about 5 minutes and screen through a 200 Mesh screen before spraying.
4. Load item #1 drug layered MCC sphere in a spray dryer (GPCG-3 fluid bed dryer). Spray #3 coating suspension at approximately 5-15 g/minutes.
5. After completing the spraying process, continue to dry the pellets for approximately 30 minutes at 40±5° C.
6. Collect the coated beads of Example 4B after sequentially screening through 40 Mesh and 100 Mesh screens to remove lumps and fines.
7. Mix the coated beads with other excipients in Example 4D (lactose, microcrystalline cellulose, gelling polymer, crospovidone and magnesium stearate) to make tablets at a target weight of approximately 500 mg at a target hardness of approximately 3-5 kp using a Stokes, Fette or Killian rotary press.

4C & 4E: Eudragit E 100 top layered pellets and tablets
1. Mix item #3, 4, and 5 (IPA, Acetone and Water) to make the solvent system.
2. Add Item #2 Eudragit E 100 into half of the solvent system from Step 1. Keep mixing until dissolved.
3. Add Items #6 and #7 (Triethyl Citrate and Talc) into the remaining half of the solvent system from Step #1 and homogenize for approximately 10 minutes.
4. Add Step #3 suspension to Step #2 solution and keep mixing. Pass the suspension through 0.5 mm sieve before spraying.
5. Load item #1 (drug layered MCC spheres) in a spray dryer (GPCG-3 fluid bed dryer). Spray step #4 coating suspension at approximately 5-15 g/minutes.
6. After completing the spray process, continue to dry the beads for approximately 30 minutes at 40±5° C.
7. Collect the coated beads of Example 4C after consecutively passing them through 40 Mesh and 100 mesh screens to remove lumps and fines.
8. Mix the coated beads with other excipients in Example 4E (lactose, microcrystalline cellulose, gelling polymer, crospovidone and magnesium stearate) and compress into tablets at a target weight of 500 mg and at a target hardness of approximately 3-5 kp using a Stokes, Fette or Killian rotary press.

Tables 4A to 4E show the formulations of Examples 4A to 4E, respectively.

TABLE 4A

|   | Ingredient | Liquid (g) | Solid (g) |
|---|---|---|---|
| 1 | MCC Sphere | | 1500 |
| 2 | Naloxone HCl Dihydrate | | 52 |
| 3 | Povidone K29/30 | | 60 |
| 4 | Water | 2888 | |
| | Total solution | 3000 | |
| | | Total solids: | 1612 |

TABLE 4B

| | Ingredient | Liquid (g) | Solid (g) |
|---|---|---|---|
| 1 | Drug Layered MCC sphere of Ex. 4A | | 500 |
| 2 | Kollicoat Smartseal 30 D | 513 | 153.8 |
| 3 | Triethyl Citrate | 23.1 | 23.1 |
| 4 | Talc | | 123 |
| 5 | Water | 1003 | |
| | Total solution | 1538 | |
| | Total solids: | | 800 |

TABLE 4C

| | Ingredient | Liquid (g) | Solid (g) |
|---|---|---|---|
| 1 | Drug Layered MCC sphere of Ex. 4A | | 700 |
| 2 | Eudragit E 100 | | 176.4 |
| 3 | IPA | 1542.6 | |
| 4 | Acetone | 1028.7 | |
| 5 | Water | 128.7 | |
| 6 | Triethyl Citrate | 35.4 | 35.4 |
| 7 | Talc | | 88.2 |
| | Total solution | 3000 | |
| | Total solids: | | 1000 |

TABLE 4D

| No. | Ingredients | mg/tab | % |
|---|---|---|---|
| 1 | Drug Layered MCC Pellets of Ex. 4B | 300.00 | 60.000 |
| 2 | Lactose Monohydrate (Fast Flo 316) | 166.00 | 33.200 |
| 3 | MCC (Avicel pH 102) | 0.00 | 0.000 |
| 4 | Pregelatinized Starch (Swelstar MX-1) | 5.00 | 1.000 |
| 5 | Crospovidone | 25.00 | 5.000 |
| 6 | Magnesium stearate | 3.75 | 0.750 |
| | Total | 500 | 100.0 |

TABLE 4E

| No. | Ingredients | mg/tab | % |
|---|---|---|---|
| 1 | Drug Layered MCC Pellets of Ex. 4C | 300.00 | 60.000 |
| 2 | Lactose Monohydrate (Fast Flo 316) | 166.00 | 33.200 |
| 3 | MCC (Avicel pH 102) | 0.00 | 0.000 |
| 4 | Pregelatinized Starch (Swelstar MX-1) | 5.00 | 1.000 |
| 5 | Crospovidone | 25.00 | 5.000 |
| 6 | Magnesium stearate | 3.75 | 0.750 |
| | Total | 500 | 100.0 |

Dissolution tests were performed on Examples 4D and 4E under the following conditions:

Method: USP apparatus II (Paddle)

Paddle speed: 75 rpm

Medium: Distilled water or 0.1N HCl

Volume: 500 mL

Sampling intervals: 5, 10, 15, 30, 45 and 60 minutes

Table 4F shows the dissolution data for Example 4D, and Table 4G shows the dissolution data for Example 4E.

TABLE 4F

| Time | Dissolution of Naloxone in different media (% Dissolved) (n = 3) | |
|---|---|---|
| (Minutes) | Water | 0.1N HCl |
| 0 | 0 | 0 |
| 5 | 43 | 44 |
| 10 | 53 | 57 |
| 15 | 61 | 62 |
| 30 | 72 | 70 |
| 45 | 75 | 74 |
| 60 | 80 | 80 |

TABLE 4G

| Time | Dissolution of Naloxone in different media (% Dissolved) (n = 3) | |
|---|---|---|
| (Minutes) | Water | 0.1N HCl |
| 0 | 0 | 0 |
| 5 | 3 | 21 |
| 10 | 9 | 47 |
| 15 | 14 | 64 |
| 30 | 26 | 81 |
| 45 | 35 | 82 |
| 60 | 40 | 85 |

Example 5A

The formulations of Formula 5A (Oxycodone HCl Tablet, USP (5 mg and 10 mg)) and 5B (Oxycodone HCl Tablets, USP (20 mg and 30 mg)) were prepared in accordance with the following general procedure:

1.: Drug Layer:

Oxycodone HCl and Povidone (PVP) are dissolved into purified water in a 50-Gallon stainless steel tank using an overhead mixer to make the drug layered coating solution. The solution is applied to MCC spheres using a GPCG-60 with an 18" Wurster insert. The resulting drug layered pellets are screened using a Sweco sifter configured with US 140 mesh and US 50 mesh screens.

2.: Polymer Coating:

A polymer coating suspension (Eudragit E PO, Sodium lauryl sulfate (SLS), Stearic acid and Talc) prepared in a 100-Gallon stainless steel tank using an overhead mixer, is applied onto Oxycodone HCl drug layered pellets using a GPCG-60 with an 18" Wurster insert. After the polymer coating is completed, the pellets are screened using a Sweco sifter configured with US 140 mesh and US 40 mesh screens.

3.: Blending:

Polymer coated pellets and excipients (Lactose Monohydrate, Crospovidone, Pregelatinized Starch (Swelstar MX-1), FD&C No. 6 Yellow (20 mg and 30 mg doses only)) are passed through a US 25 mesh screen into a 10 Cu. Ft. V-Blender and mixed for 10 minutes. Magnesium Stearate is passed through a US 30 mesh screen into the V-blender and lubricated for 3 minutes to make the final blend.

4.: Compression:

The final blend is compressed into required tablet strengths using a Manesty 700 Rotary Tablet Press.

Tables 5A and 5B show the formulations for Formulations 5 A and 5B, respectively.

TABLE 5A

Formula 5A: Oxycodone HCl Tablet, USP (5-15 mg)

| No. | Ingredients | Percentage (%) | Quantity per batch per | Quantity per Tablet (mg) | | | |
|---|---|---|---|---|---|---|---|
| | | | | 5 mg | 7.5 mg | 10 mg | 15 mg |
| 1 | Oxycodone HCl, USP | 2.00 | 2.5 | 5 | 7.5 | 10 | 15 |
| 2 | MCC Sphere (100-200 um) | 34.12 | 42.65 | 85.30 | 127.95 | 170.60 | 255.90 |
| 3 | Povidone K29/32, USP | 1.36 | 1.70 | 3.40 | 5.10 | 6.80 | 10.20 |
| 4 | Eudragit E PO | 9.64 | 12.05 | 24.10 | 36.15 | 48.20 | 72.30 |
| 5 | Sodium Lauryl Sulfate | 0.97 | 1.21 | 2:43 | 3.64 | 4.85 | 7.28 |
| 6 | Stearic acid | 1.45 | 1.81 | 3.63 | 5.44 | 7.25 | 10.88 |
| 7 | Talc | 4.81 | 6.01 | 12.03 | 18.04 | 24.05 | 36.08 |
| 8 | Lactose Monohydrate | 28.90 | 36.13 | 72.25 | 108.38 | 144.50 | 216.75 |
| 9 | Crospovidone | 15.00 | 18.75 | 37.50 | 56.25 | 75.00 | 112.50 |
| 10 | Swelstar MX-1 | 1.00 | 1.25 | 2.50 | 3.75 | 5.00 | 7.50 |
| 11 | Magnesium Stearate, NF | 0.75 | 0.94 | 1.88 | 2.81 | 3.75 | 5.63 |
| | Total weight | 100 | 125 | 250 | 375 | 500 | 750 |

TABLE 5B

Formula 5B: Oxycodone HCl Tablets, USP (20-30 mg)

| No. | Ingredients | Percentage (%) | Quantity per, batch (kg) | Quantity per Tablet (mg) | |
|---|---|---|---|---|---|
| | | | | 20 mg | 30 mg |
| 1 | Oxycodone HCl, USP | 4.00 | 5.00 | 20 | 30 |
| 2 | MCC Sphere (100-200 um) | 32.14 | 40.18 | 160.70 | 241.05 |
| 3 | Povidone K29/32, USP | 1.29 | 1.61 | 6.45 | 9.68 |
| 4 | Eudragit E PO | 9.64 | 12.05 | 48.20 | 72.30 |
| 5 | Sodium Lauryl Sulfate | 0.97 | 1.21 | 4.85 | 7.28 |
| 6 | Stearic acid | 1.45 | 1.81 | 7.25 | 10.88 |
| 7 | Talc | 4.81 | 6.01 | 24.05 | 36.08 |
| 8 | Lactose Monohydrate | 28.90 | 36.13 | 144.50 | 216.75 |
| 9 | Crospovidone | 15.00 | 18.75 | 75.00 | 112.50 |
| 10 | Swelstar MX-1 | 1.00 | 1.25 | 5.00 | 7.500 |
| 11 | FD&C No. 6 Yellow | 0.05 | 0.06 | 0.25 | 0.38 |
| 12 | Magnesium Stearate, NF | 0.75 | 0.94 | 3.75 | 5.63 |
| | Total weight | 100 | 125 | 500 | 750 |

Example 5B

Dissolution was tested on Formulation 5 A (15 mg tablets) under the following conditions:

Method: USP apparatus II (Paddle)

Paddle speed: 50 rpm

Medium: 0.1N HCl

Volume: 900 mL

Sampling intervals: 5, 10, 15, 30, 45 and 60 minutes

Table 5C below shows the dissolution data of Formulation 5 A (15 mg) in 0.1N HCl.

TABLE 5C

Dissolution Profile of Prototype Oxycodone HCl Formulation, 15 mg Tablets in 0.1N HCl

| Sample Description | % Oxycodone HCl Dissolved | | | | | |
|---|---|---|---|---|---|---|
| | 5 | 10 | 15 | 30 | 45 | 60 |
| Tablet 1 | 80 | 98 | 100 | 101 | 102 | 103 |
| Tablet 2 | 76 | 87 | 89 | 92 | 94 | 95 |
| Tablet 3 | 71 | 85 | 87 | 89 | 91 | 94 |
| Tablet 4 | 80 | 98 | 99 | 100 | 101 | 101 |
| Tablet 5 | 72 | 88 | 90 | 94 | 96 | 97 |
| Tablet 6 | 66 | 87 | 89 | 92 | 94 | 95 |
| Ave | 74 | 91 | 92 | 95 | 96 | 98 |
| RSD | 7.4 | 6.5 | 6.1 | 5.1 | 4.5 | 3.8 |

Example 5C

Eighteen healthy subjects (8 male, 10 female) were enrolled and randomized to receive the Formulation 5 A (15 mg) and 17 (94.4%) subjects completed the study as planned. Seventeen (94.4%) subjects received their assigned dose of test study drug and 18 (100%) subjects received their assigned dose of reference study drug. Eighteen subjects were included in the safety population, and 17 subjects were included in the pharmacokinetic (PK) population.

Demographics: Subjects were representative of a healthy adult male and female population, ranging from 18 to 43 years of age. Overall mean (SD) age was 29.6 (7.78) years and mean (SD) Body mass index (BMI) was 26.5 (2.64) kg/m2. Racial composition was 10 (55.6%) Black and 8 (44.4%) White.

Methodology: This was a single-center, randomized, open-label, single-dose, two-period, crossover study to assess the pharmacokinetics (PK) and relative bioavailability of single doses of a test (T) formulation of oxycodone HCl immediate-release (IR) 15 mg tablets (Formula 5A) and Roxicodone® 15 mg tablets (Reference Drug) (R) in healthy adult male and female subjects under fed conditions. Each subject was randomized to one of two treatment sequences (T-R, R-T) according to a randomization schedule prepared prior to the start of the study.

There was a 7-day washout between each single dose administration. Subjects were dosed on the same day for Day 1 of Period 1, and crossed over to an alternate formulation to be dosed on the same day for Day 8 of Period 2.

Subjects received a single dose of naltrexone 50 mg with approximately 240 mL room temperature water 12 hours (±1 hour) and one hour (±10 minutes) prior to, and 12 hours (±30 minutes) after receiving each study drug dose during Periods 1 and 2.

Following an overnight fast of at least 10 hours, subjects completed a high fat breakfast within approximately 5 minutes prior to dosing. Subjects then received a single oral dose of the reference or test formulation with approximately 240 mL room temperature water at approximately 0800 hours (t 1 hour).

Serial blood samples for determination of oxycodone plasma concentrations and PK analysis were obtained on Day 1 at time 0 (within 90 minutes pre-dose) and 0.5, 1, 1.5, 2, 2.5, 3, 4, 6, 8, 10, 12, 16, 24 and 36 hours post-dose. Subjects were discharged from the research facility approximately 36 hours after receiving their dose of study drug. During Period 2, Day 8 following a washout period of 7 days, subjects crossed over to an alternate formulation and the same procedures were performed.

Subjects completing both treatment periods with no major protocol violations and providing plasma drug concentration data were included in the PK analysis population. Plasma oxycodone concentration levels are listed and summarized using descriptive statistics. PK parameters ($AUC_{0-t}$, $AUC_{0-inf}$, $C_{max}$, $t_{max}$, $t_{1/2}$, and $K_{el}$) of plasma oxycodone are listed and summarized by treatment. Relative bioavailability of the test and reference formulations was determined based on $AUC_{0-inf}$, $AUC_{0-inf}$ and $C_{max}$ of oxycodone. Log-transformed PK parameters $AUC_{0-t}$, $AUC_{0-inf}$ and $C_{max}$ were analyzed using analysis of variance (ANOVA) including terms for sequence, formulation, and period as fixed effects, and subject nested within sequence as a random effect. The arithmetic means, geometric means, ratio of the geometric means and 90% confidence intervals (CIs) on the ratio of test to reference study drug are displayed.

Figure 4:
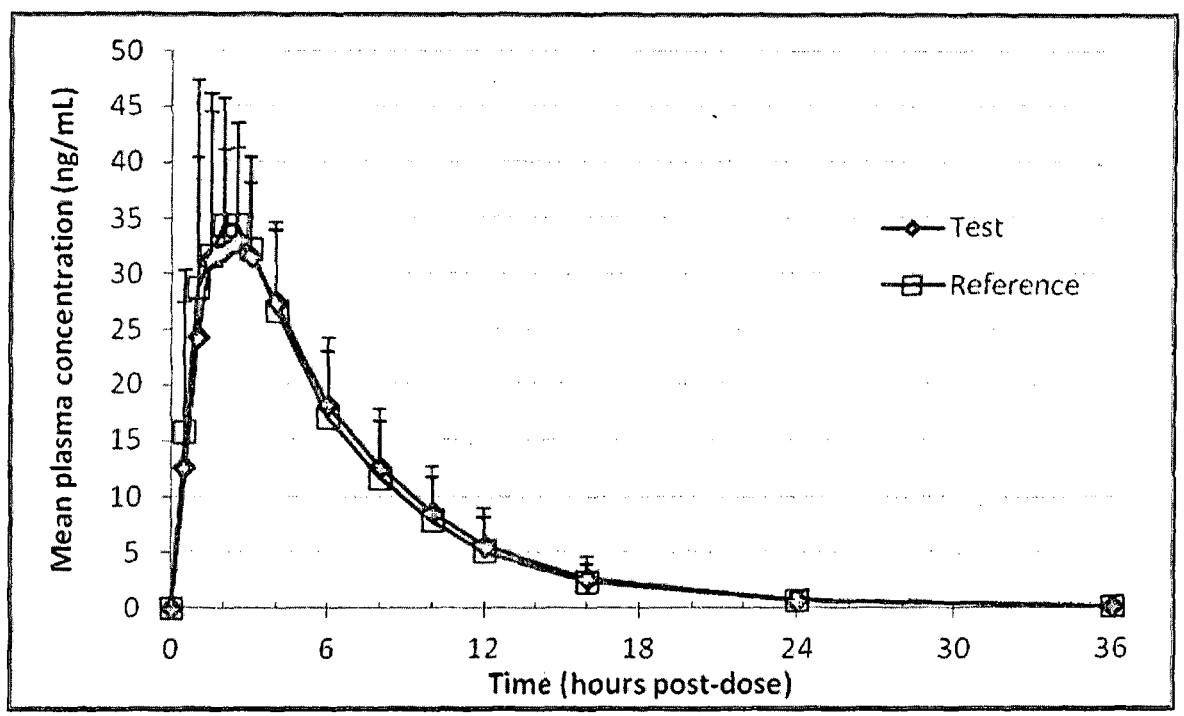
FIG. 4 is a graphical depiction of the pharmacokinetic results from Example 5.

Plots of mean concentration levels of plasma oxycodone versus time were generated for each treatment group and are shown in FIG. 4 and Table 5D below.

TABLE 5D

| Parameter | Geometric means | | Ratio (T/R) | 90% C.I. (T/R) |
| --- | --- | --- | --- | --- |
| | Test | Reference | | |
| $C_{max}$ (ng/mL) | 40.88 | 40.51 | 1.01 | (92.14, 110.56) |
| $AUC_{0-t}$ (ng*h/mL) | 245.28 | 237.01 | 1.03 | (99.04, 108.14) |
| $AUC_{0-inf}$ (ng*h/mL) | 246.32 | 238.16 | 1.03 | (98.99, 108.06) |

The results from the pharmacokinetic parameters for the PK population are shown in Table 5E below.

TABLE 5E

| | | Treatment Group | |
| --- | --- | --- | --- |
| Parameter (unit) | Statistic | Test N = 17 | Reference N = 17 |
| $C_{max}$ (ng/mL) | Mean (SD) | 41.7 (8.39) | 42.4 (12.11) |
| $AUC_{0-t}$ (ng*h/mL) | Mean (SD) | 252 (53.4) | 248 (74.0) |
| $AUC_{0-inf}$ (ng*h/mL) | Mean (SD) | 253 (53.9) | 249 (74.5) |

TABLE 5E-continued

| | | Treatment Group | |
| --- | --- | --- | --- |
| Parameter (unit) | Statistic | Test N = 17 | Reference N = 17 |
| $t_{max}$ (h) | Median (Range) | 2.50 (0.50-6.00) | 2.00 (0.50-4.00) |
| $t_{1/2}$ (h) | Mean (SD) | 4.78 (0.580) | 4.66 (0.647) |
| $K_{el}$ (1/h) | Mean (SD) | 0.147 (0.0184) | 0.152 (0.0234) |

The dissolution and pharmacokinetic results suggest the dosage form is identical in drug release rates compared with the reference drug product.

Example 6

Formulations 6A (Drug Layered Granules), 6B (Eudragit E PO® coated Granules), and 6C (Tablets) were prepared in accordance with the following general procedure:

Procedure for Formulation 6A: Drug layer coating
  Dissolve item #3 (povidone) into item #4 (water) to make a binder solution, and add item #2 (naloxone) into the binder solution to prepare a coating solution.
  Spray the above coating solution onto item #1 (acetaminophen (APAP) Granules) using an appropriate spray dryer such as a Model GPCG-3 from Glatt Techniques.

Procedure for Formulation 6B: Eudragit E PO top layered Naloxone-APAP Granules (45% weight gain)
  1. Use the drug layered APAP Granules as described in 5A for further coating.
  2. Add item #3 and 4 (sodium lauryl sulfate (SLS) and Stearic acid) into item #6 (water) and keep mixing until dissolution.
  3. Add item #2 (Eudragit E PO) into the above solution, keep mixing until a yellowish solution forms.
  4. Add item #5 (Talc) into the above polymer solution and keep mixing for at least 30 minutes.
  5. Load item #1 (drug layered APAP Granules) into a GPCG-3 fluid bed dryer, set up the machine and spray step #3 (coating suspension) at 5-15 g/minute. Collect samples as necessary.
  6. After completing the spray process, continue to dry the granules for around 15 minutes at around 40±5° C.
  7. Collect the coated granules after passing through 40 mesh and 140 mesh screens to remove lumps and fines.

Procedure for Formulation 6C: Tablet containing Eudragit E PO top layered Naloxone-APAP Granules
  1. Pass items #1-4 (Coated Naloxone-APAP Granules, Lactose, Pregelatinized Starch and Crospovidone) through a 20 Mesh screen and mix for 10 minutes.
  2. Pass item #5 (Magnesium Stearate) through a 30 Mesh screen into the above blend and mix for about 3 minutes.
  3. Compress into caplet shaped tablets at a target weight of about 750 mg and a target hardness of about 5-10 kp.

Tables 6A to 6C show the formulations for Formulations 6A to 6C, respectively. Table 6D shows the amounts of pregelatinized starch and crospovidone in various formulations prepared in accordance with Example 6C.

TABLE 6A

| | Ingredient | Liquid (g) | Solid (g) |
| --- | --- | --- | --- |
| 1 | APAP (Granules) | | 722.22 |
| 2 | Naloxone HCl Dihydrate | | 12.2 |

TABLE 6A-continued

| | Ingredient | Liquid (g) | Solid (g) |
|---|---|---|---|
| 3 | Povidone K29/30 | | 27.8 |
| 4 | Water | 1390 | |
| | Total solution | 1430 | |
| | Total solids: | | 762.22 |

TABLE 6B

| | Ingredient | Lot | Liquid (g) | Solid (g) |
|---|---|---|---|---|
| 1 | Drug Layered APAP | Example 6A | | 381.11 |
| 2 | Eudragit E PO | | | 97.98 |
| 3 | SLS | | | 9.83 |
| 4 | Stearic acid | | | 14.75 |
| 5 | Talc | | | 48.93 |
| 6 | Water | | 971 | |
| | Total solution | | 1143 | |
| | Total solids: | | | 552.6 |

TABLE 6C

| No. | Ingredients | mg/tab | Qty/Batch (g.) | % |
|---|---|---|---|---|
| 1 | Eudragit E PO coated Naloxone-APAP Granules | 552.75 | 11.055 | 73.7 |
| 2 | Lactose Monohydrate (Fast Flo 316) | 41.625-146.625 | 0.833-2.933 | 5.55-19.55 |
| 3 | Pregelatinized Starch (Swelstar MX-1) | 7.5-37.5 | 0.15-0.75 | 1-5 |
| 4 | Crospovidone | 37.5-112.5 | 0.75-2.25 | 5-15 |
| 5 | Magnesium stearate | 5.625 | 0.11 | 0.75 |
| | Total | 750 | 15 | 100.0 |

TABLE 6D

| Ref. No. | % Pregelatinized Starch (Swelstar MX-1) | % Crospovidone |
|---|---|---|
| 1 | 0 | 5 |
| 2 | 1 | 5 |
| 3 | 1 | 15 |
| 4 | 2.5 | 5 |
| 5 | 2.5 | 15 |
| 6 | 5 | 5 |
| 7 | 5 | 15 |

Example 7

Formulation 7 was prepared in accordance with the following general procedure:
Procedure:
1. Pass items #1-5 (Naloxone, APAP, Lactose, Pregelatinized Starch and Crospovidone) through a 20 Mesh screen and mix for about 10 minutes.
2. Pass item #6 (Magnesium Stearate) through a 30 Mesh screen into the above blend and mix for about 3 minutes.
3. Compress into caplet shaped tablets at a target weight of about 750 mg and a target hardness of about 5-10 kp.

Table 7 shows the formulation for Formulation 7. Table 7A shows the amounts of pregelatinized starch and crospovidone in various formulations prepared in accordance with Example 7.

TABLE 7

| No. | Ingredients | mg/tab | Qty/Batch (g.) | % |
|---|---|---|---|---|
| 1 | Naloxone HCl Dihydrate | 6.10 | 0.122 | 0.813 |
| 2 | APAP (Granules) | 361.11 | 7.22 | 48.15 |
| 3 | Lactose Monohydrate (Fast Flo 316) | 227.25-332.25 | 4.545-6.645 | 30.3-44.3 |
| 4 | Pregelatinized Starch (Swelstar MX-1) | 7.5-37.5 | 0.15-0.75 | 1-5 |
| 5 | Crospovidone | 37.5-112.5 | 0.75-2.25 | 5-15 |
| 6 | Magnesium stearate | 5.625 | 0.11 | 0.75 |
| | Total | 750 | 15 | 100.0 |

TABLE 7A

| Ref. No. | % Pregelatinized Starch (Swelstar MX-1) | % Crospovidone |
|---|---|---|
| 8 | 0 | 5 |
| 9 | 1 | 5 |
| 10 | 1 | 15 |
| 11 | 2.5 | 5 |
| 12 | 2.5 | 15 |
| 13 | 5 | 5 |
| 14 | 5 | 15 |

Example 8

Figure 5:
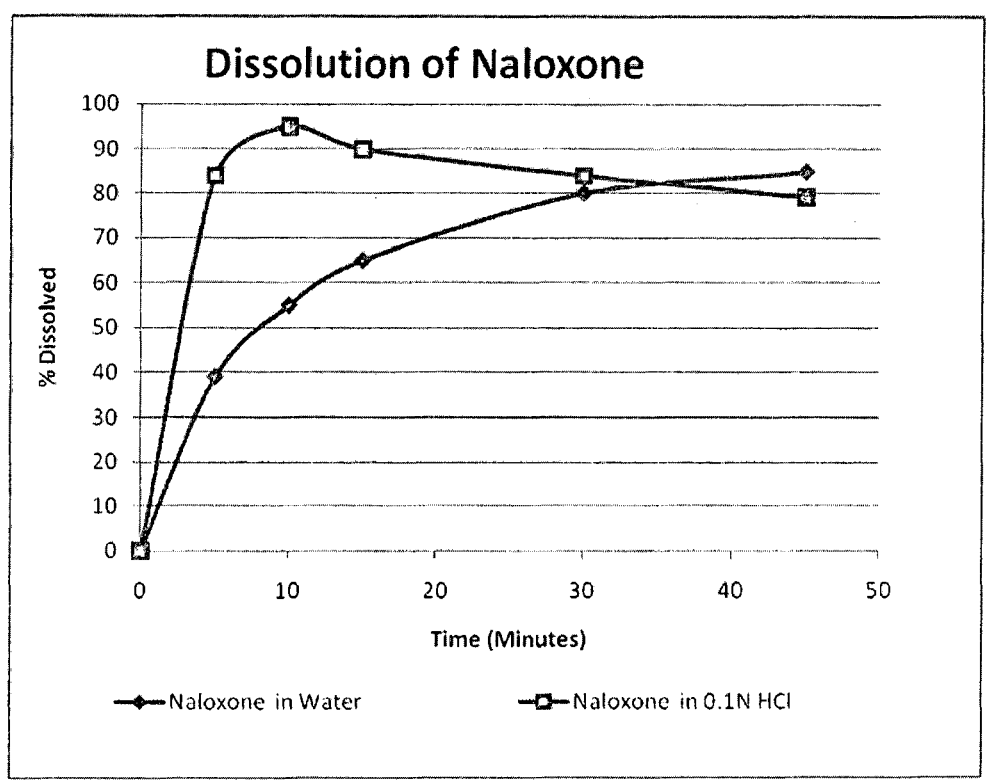
FIG. 5 is a graphical depiction of the dissolution data of Formulation 6B from Example 8.
Figure 6:
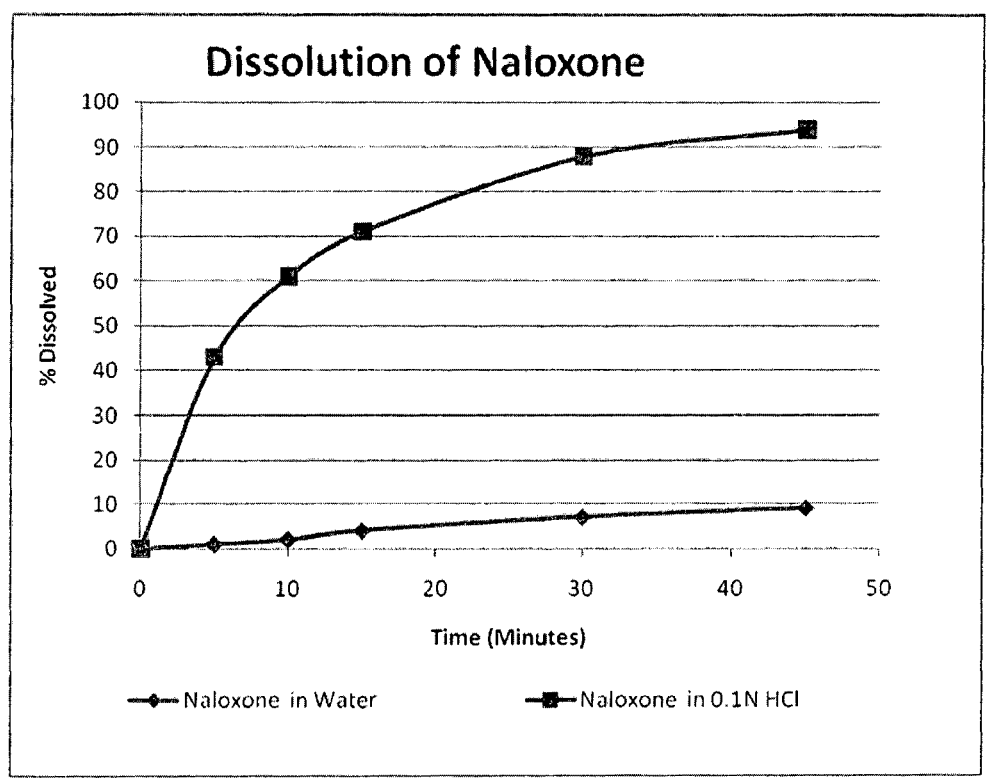
FIG. 6 is a graphical depiction of the dissolution data of Formulation 6C from Example 8.
Figure 7:
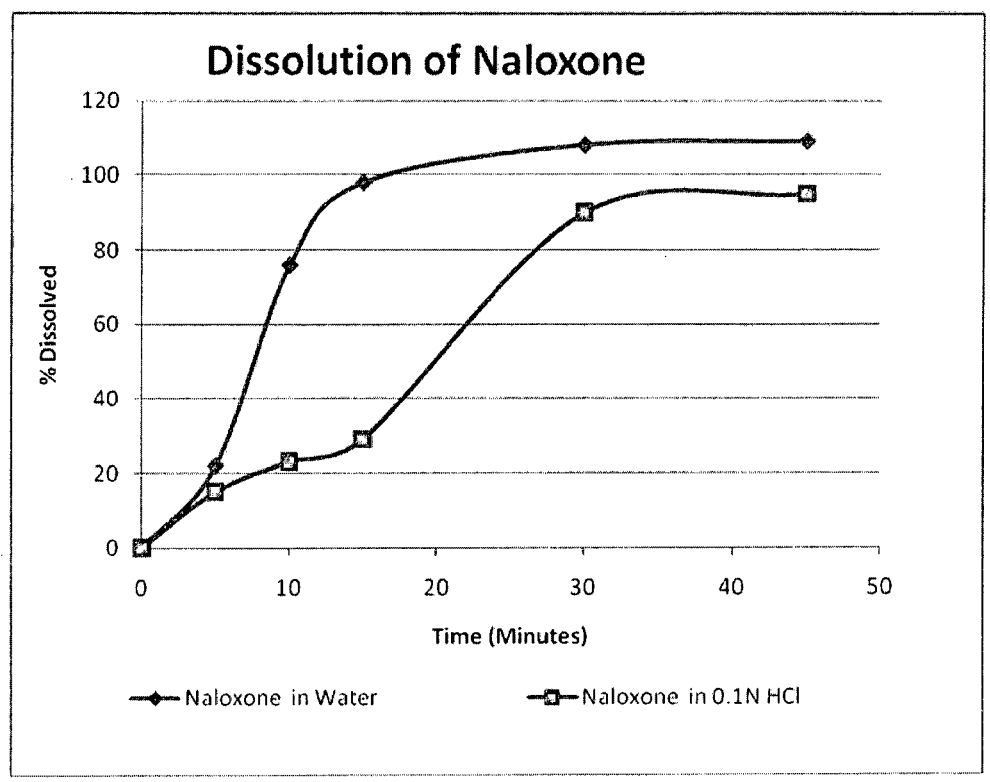
FIG. 7 is a graphical depiction of the dissolution data of Formulation 7 from Example 8.
Figure 8:
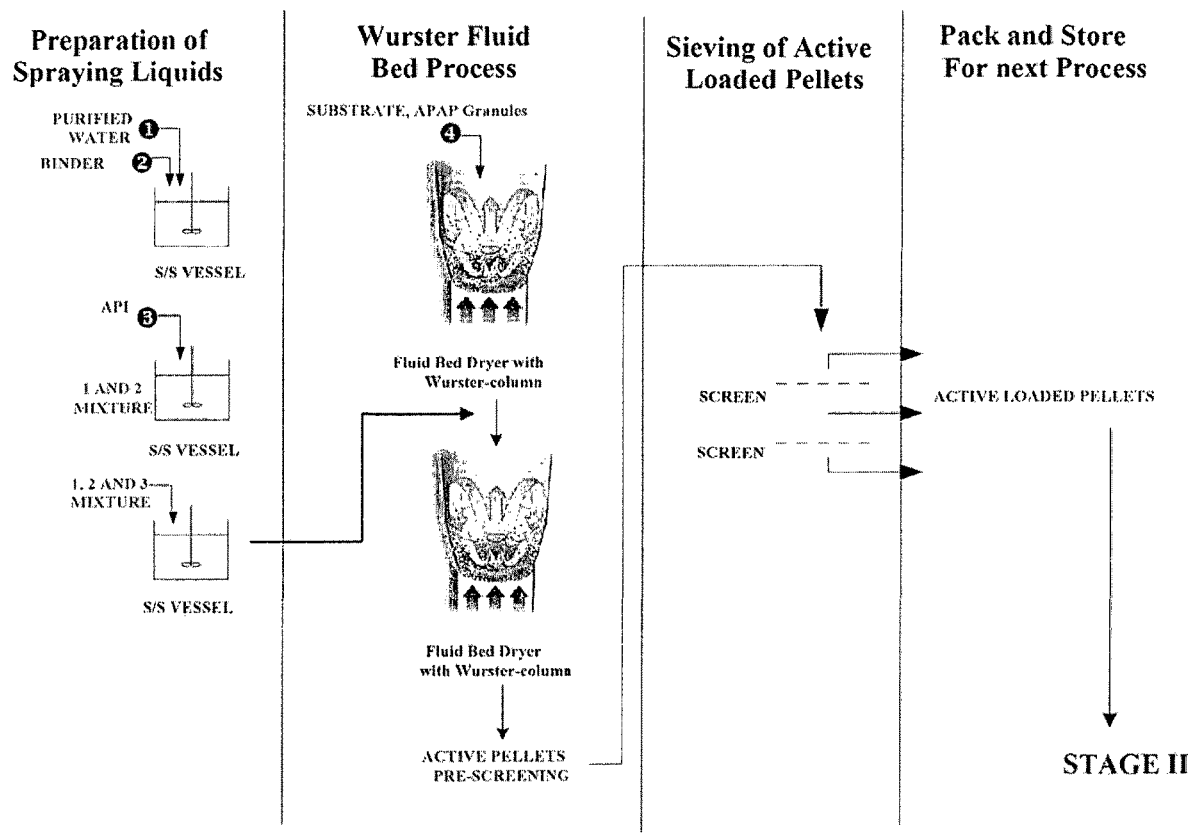
FIG. 8 is a flow chart of a manufacturing process for layering a first active agent with a second active agent.
Figure 9:
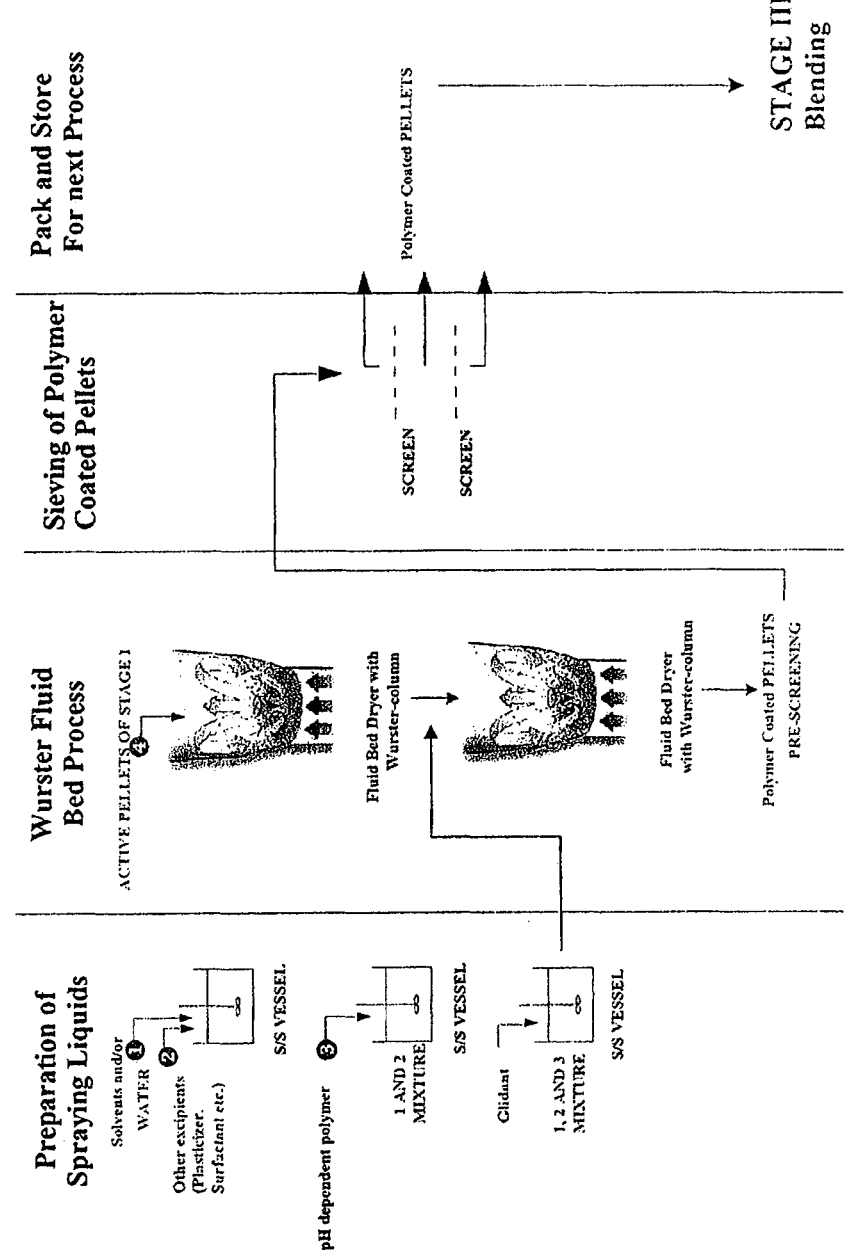
FIG. 9 is a flow chart of a manufacturing process for layering a material sensitive to acidic pH on substrates in accordance with an embodiment of the invention.
Figure 10:
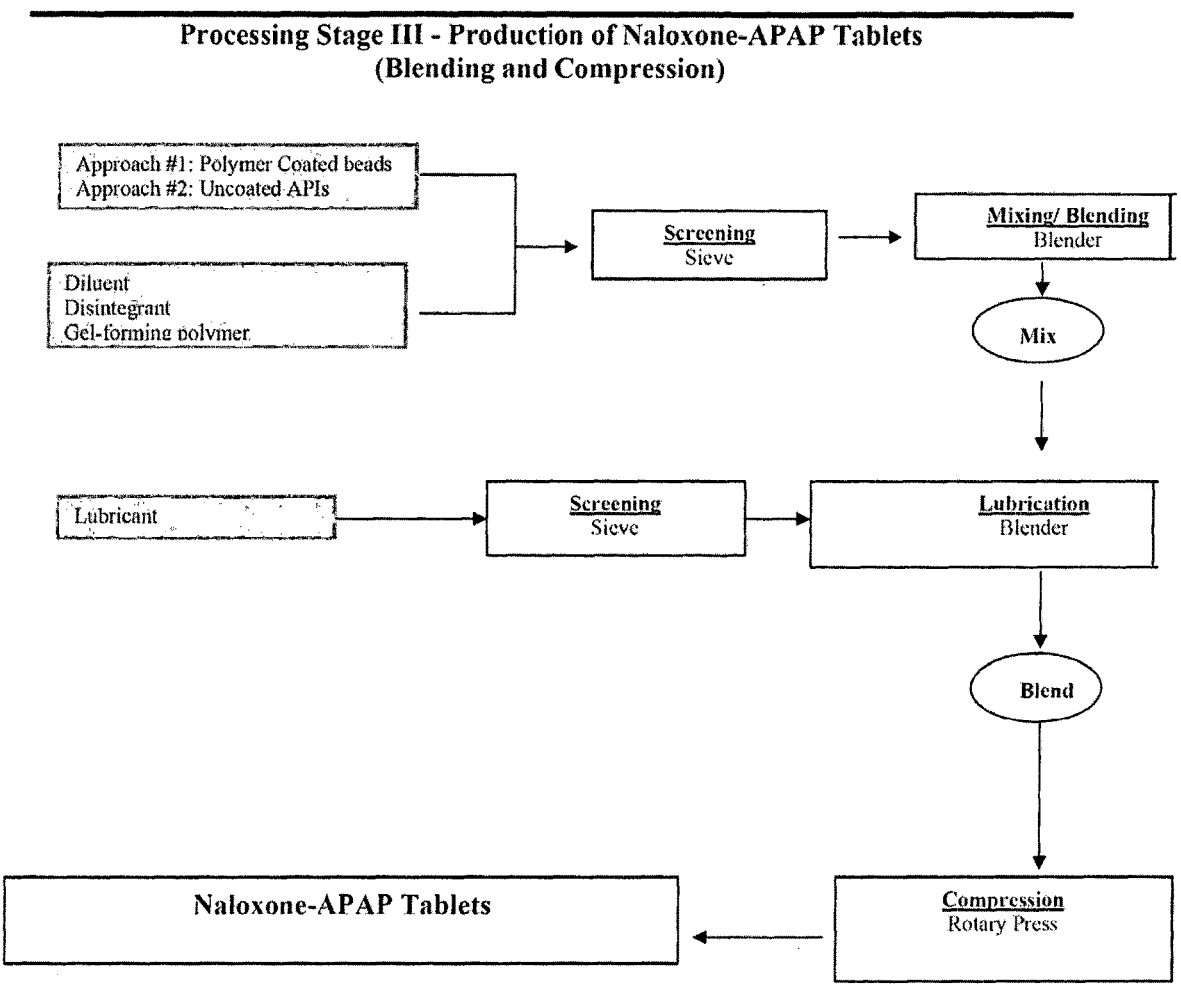
FIG. 10 is a flow chart of a manufacturing process for preparing a tablet in accordance with an embodiment of the invention.

Dissolution was tested on Formulation 6B, Formulation 6C and Formulation 7 under the following conditions:
Method: USP apparatus 2 (Paddle)
Paddle speed: 50 rpm
Medium: Distilled water or 0.1N HCl
Volume: 900 mL
Sampling intervals: 5, 10, 15, 30, and 45 minutes Tables 8A, 8B and 8C below (and FIGS. 5, 6 and 7) show the dissolution data of Formulations 6B, 6C and 7 in both water and 0.1N HCl.

TABLE 8A (Formulation 6B: Eudragit E PO coated Naloxone-APAP Granules)

| | Dissolution of Naloxone-APAP in different media (%) (n = 1) | |
|---|---|---|
| Time | Naloxone | |
| (Minutes) | Water | 0.1N HCl |
| 0 | 0 | 0 |
| 5 | 39 | 84 |
| 10 | 55 | 95 |
| 15 | 65 | 90 |
| 30 | 80 | 84 |
| 45 | 85 | 79 |

Polymer Eudragit E PO coated Naloxone loaded APAP Granules (Formulation 6B) showed pH dependent dissolution profiles for Naloxone in varying dissolution media. Dissolution in 0.1N HCl releases >80% of Naloxone within 5 minutes. Dissolution in water is slower for Naloxone than in 0.1N HCl

TABLE 8B (Formulation 6C: Formulation containing Eudragit E PO coated Naloxone-APAP Granules, 1% Swelstar and 5% Crospovidone)

| Time | Dissolution of Naloxone-APAP in different media (%) (n = 1) Naloxone | |
|---|---|---|
| (Minutes) | Water | 0.1N HCl |
| 0 | 0 | 0 |
| 5 | 1 | 43 |
| 10 | 2 | 61 |
| 15 | 4 | 71 |
| 30 | 7 | 88 |
| 45 | 9 | 94 |

Formulation 6C was prepared using coated Naloxone-APAP beads (Formulation 6B), 1% Swelstar, 5% Crospovidone and other excipients. The dissolution in 0.1N HCl reaches 94% of Naloxone at 45 minutes. In water however, the dissolution study shows a release of 9% of Naloxone at 45 minutes.

TABLE 8C (Formulation 7: Formulation containing uncoated Naloxone, APAP Granules, 5% Swelstar and 5% Crospovidone)

| Time | Dissolution of Naloxone-APAP in different media (%) (n = 1) Naloxone | |
|---|---|---|
| (Minutes) | Water | 0.1N HCl |
| 0 | 0 | 0 |
| 5 | 22 | 15 |
| 10 | 76 | 23 |
| 15 | 98 | 29 |
| 30 | 108 | 90 |
| 45 | 109 | 95 |

Formulation 7 was prepared using uncoated active agents (Naloxone and APAP), 5% Swelstar, 5% Crospovidone and other excipients. The dissolution in 0.1N HCl is slower than in water for Naloxone and suggests the gelling polymer alone may not be satisfactory enough to impart abuse deterrent properties based on preferential dissolution to the opioid combination drug product.

Example 9

Syringability and extractability of Oxycodone HCl Abuse-Deterrent Immediate Release tablets (Example 5A) of the present invention against Reference Listed Drug (RLD) product, Roxicodone® tablet (15 mg) were evaluated. Roxicodone is a commercially available oxycodone hydrochloride immediate release tablets.

Materials and Equipment:
Small weigh boat
5 mL syringe
20 mL scintillation vial
Cotton
27&½ G needle
Clear glass mortar & pestle
Timer Procedure:
Tablets were ground/blended using following method:
1. One (1) tablet or powder blend equivalence to one tablet was placed in a 2 oz. glass mortar.
2. The tablet was crushed and ground or blended 6-7 times using a glass pestle to break up the tablet or blend into small pieces.
3. The timer was started the pieces were ground using vigorous circular motions.
4. The material from the sides of the mortar was brought to the bottom by tapping the mortar on the counter while grinding.
5. Grinding continued for 1 minute to form a uniform fine powder.

5 mL of appropriate extraction solvent was added to the vial and the timer started while shaking by hand for 30 seconds and then poured into a small weigh boat containing a pea-size piece of cotton. Using a 27&½ gauge needle and a 5 mL syringe, an attempt to syringe as much liquid as possible through the cotton was conducted and the volume aspirated during a 5 minute period (T0 sample) was recorded. Aspirated samples were submitted for assay. In cases of heated/boiled samples, the same instructions were followed above with heating the solution while shaking until it just starts to boil, then pour out into weigh boat containing cotton.

For the 10 minute time point (T10 sample): the same procedure as above was followed and the sampled boiled. Samples were allowed to remain in vial for 10 minutes before aspirating.

Extraction solvents used were Tap Water, Vinegar, 0.9% Saline and 40% Ethanol.

Results:

The following tables show the syringability and extraction study results on Oxycodone HCl Tablets 15 mg in different medium.

TABLE 9A

Syringability and Extraction study on Oxycodone HCl Tablets in Tap water (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 4.6 | 77.4 | Not needed; T0 exceeds Q value in Specifications | Not needed; T0 exceeds Q value in Specifications |
| Example 5A, 15 mg | .4 | 8.44 | 3.60 | 28.57 |

TABLE 9B

Syringability and Extraction study on Oxycodone HCl Tablets in Vinegar (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 4.5 | 80.0 | Not needed; T0 exceeds Q value in Specifications | Not needed; T0 exceeds Q value in Specifications |
| Example 5A, 15 mg | 0.15 | 4.42 | 3.10 | 46.83 |

TABLE 9C

Syringability and Extraction study on Oxycodone HCl Tablets in 40% EtOH (n = 2)

| Sample | T0 Extraction volume (ml) | T0 Oxycodone extracted (%) | T10 Extraction volume (ml) | T10 Oxycodone extracted (%) |
|---|---|---|---|---|
| Roxicodone 15 mg tablets (RLD) | 3.6 | 59.7 | Not performed | Not performed |
| Example 5A, 15 mg | 0.20 | 3.36 | 3.15 | 38.04 |

TABLE 9D

Syringability and Extraction study on Oxycodone HCl Tablets in 0.9% Saline (n = 2)

| Sample | T0 Extraction volume (ml) | T0 Oxycodone extracted (%) | T10 Extraction volume (ml) | T10 Oxycodone extracted (%) |
|---|---|---|---|---|
| Roxicodone 15 mg tablets (RLD) | 4.5 | 79.8 | Not needed; T0 exceeds Q value in Specifications | Not needed; T0 exceeds Q value in Specifications |
| Example 5A, 15 mg | 0.85 | 3.78 | 1.80 | 15.30 |

Test formulation (Example 5A, 15 mg) significantly improved both syringability and extractability compared with reference product (Roxicodone 15 mg) at T0 time point. The extraction volumes in different media were reduced from about 3.6-4.6 ml to a range of 0.15-1.4 ml. Oxycodone extractions were also reduced from range of about 59.7-80.0% to range a range of 3.36-8.44%.

Example 10

Optimization Experiments

Example 10A

Syringability and extractability of 15 mg Naloxone HCl Blend (High dose Naloxone pellets with 1% Swelstar and 0.5% Xanthan Gum) was evaluated. The formulation was prepared in accordance with the above procedures (replacing a portion of Swelstar with Xanthan Gum) and is set forth in Table 10 below.

TABLE 10

Table: Example 10A: Naloxone Tablets (15 mg)

| No. | Ingredients | Percentage (%) | Quantity per batch (g) | Quantity per Tablet (mg) |
|---|---|---|---|---|
| 1 | Naloxone HCl | 3.66 | 0.55 | 18.3 |
| 2 | MCC Sphere (100-200 um) | 35.18 | 5.28 | 175.90 |
| 3 | Povidone K29/32, USP | 1.41 | 0.21 | 7.05 |
| 4 | Eudragit E PO | 13.8 | 2.07 | 69 |
| 5 | Sodium Lauryl Sulfate | 1.38 | 0.21 | 6.9 |
| 6 | Stearic acid | 2.08 | 0.31 | 10.4 |
| 7 | Talc | 6.84 | 1.03 | 34.2 |
| 8 | Lactose Monohydrate | 18.35 | 2.75 | 91.75 |
| 9 | Crospovidone | 15.00 | 2.25 | 75 |
| 10 | Swelstar MX-1 | 1.00 | 0.15 | 5 |
| 11 | Xanthan Gum | 0.50 | 0.08 | 2.5 |
| 12 | Cab-O-Sil | 0.50 | 0.08 | 2.5 |
| 13 | FD&C No. 6 Yellow | 0.05 | 0.01 | 0.25 |
| 14 | Magnesium Stearate, NF | 0.25 | 0.04 | 1.25 |
| | Total weight | 100 | 15 | 500 |

Results were shown in Table 10A below.

TABLE 10A

Syringability and Extraction study on the Naloxone HCl Tablets (60% weight gain of Eudragit EPO and 0.5% Xanthan gum) in different extraction media at T0 (n = 2)

| Sample/Medium | Tap Water Extraction volume (ml) | Tap Water Naloxone extracted (%) | 0.9% Saline Extraction volume (ml) | 0.9% Saline Naloxone extracted (%) |
|---|---|---|---|---|
| Ex. 10A | 0.7 | 5.5 | 1.6 | 11.2 |

Figure 11:
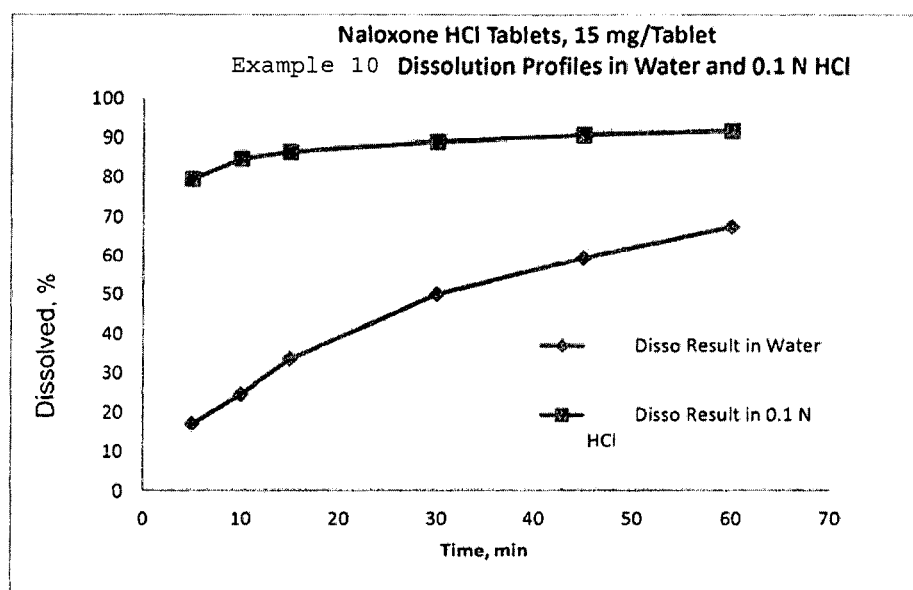
FIG. 11 is a graphical depiction of the dissolution data for Example 10.

Dissolution profiles of naloxone as a surrogate in this formulation are shown in FIG. 11. Dissolution media and conditions were as follows: 500 ml Media, USP Apparatus 2 (Paddle), at 50 RPM. Drug loading was approximately 90% of the theoretical amount in tablets.

The formulations yield results demonstrating the use of a higher loading of the acid sensitive polymer Eudragit EPO at 60% and inclusion of 0.5% Xanthan Gum, coupled with the standard 1% Swelstar dramatically reduces extraction amounts of the opioid drug consistent with very low syringability results compared to other formulations as summarized below.

Example 10B

Syringability and extractability of 20 mg Oxycodone HCl Blend (High dose Oxycodone pellets with different concentration of Swelstar) was evaluated. Results are shown in Tables 10B-10E below. The blends were prepared in accordance with example 5B except for the compression step.

TABLE 10B

Syringability and Extraction study on 20 mg oxycodone HCl blend in Tap water (n = 2)

| Sample | T0 Extraction volume (ml) | T0 Oxycodone extracted (%) | T10 Extraction volume (ml) | T10 Oxycodone extracted (%) |
|---|---|---|---|---|
| Oxycodone Blend (1.0% Swelstar) | 3.3 | 21.62 | 1.6 | 25.66 |
| Oxycodone Blend (1.5% Swelstar) | 2.0 | 10.58 | 1.3 | 16.32 |
| Oxycodone Blend (2.0% Swelstar) | 2.5 | 7.80 | 2.0 | 25.90 |

TABLE 10C

Syringability and Extraction study on 20 mg Oxycodone HCl blend in vinegar (n = 2)

| | T0 | | T10 | |
|---|---|---|---|---|
| Sample | Extraction volume (ml) | Oxycodone extracted (%) | Extraction volume (ml) | Oxycodone extracted (%) |
| Oxycodone Blend (1.0% Swelstar) | 0.2 | 147 | 1.0 | 22.16 |
| Oxycodone Blend (1.5% Swelstar) | 1.6 | 28.44 | 1.3 | 26.26 |
| Oxycodone Blend (2.0% Swelstar) | 1.1 | 21.5 | 0.6 | 13.10 |

TABLE 10D

Syringability and Extraction of 20 mg Oxycodone HCl blends in 40% EtOH (n = 2)

| | T0 | | T10 | |
|---|---|---|---|---|
| Sample | Extraction volume (ml) | Oxycodone extracted (%) | Extraction volume (ml) | Oxycodone extracted (%) |
| Oxycodone Blend (1.0% Swelstar) | 2.3 | 37.19 | 1.3 | 23.51 |
| Oxycodone Blend (1.5% Swelstar) | 2.2 | 30.53 | 1.4 | 28.54 |
| Oxycodone Blend (2.0% Swelstar) | 1.2 | 15.80 | 1.5 | 27.30 |

TABLE 10E

Syringability and Extraction study on 20 mg Oxycodone HCl blend in 0.9% Saline (n = 2)

| | T0 | | T10 | |
|---|---|---|---|---|
| Sample | Extraction volume (ml) | Oxycodone extracted (%) | Extraction volume (ml) | Oxycodone extracted (%) |
| Oxycodone Blend (1.0% Swelstar) | 2.3 | 5.10 | 2.3 | 21.2 |
| Oxycodone Blend (1.5% Swelstar) | 2.0 | 4.19 | 2.0 | 22.38 |
| Oxycodone Blend (2.0% Swelstar) | 2.3 | 5.50 | 2.3 | 27.20 |

Example 10C

The following tables, Table 10F-10I show the syringability and extraction results on Oxycodone HCl Tablets in different extraction media. The tablets were prepared in accordance with Example 5B with the addition of 0.5% silicone dioxide (Cab-o-Sil®) and a corresponding reduction in magnesium stearate.

TABLE 10F

Syringability and Extraction study on Oxycodone HCl Tablets in Tap water (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 4.6 | 77.4 | Not needed; T0 exceeds Q value in Specifications | Not needed; T0 exceeds Q value in Specifications |
| Example 5A, 15 mg | 1.4 | 8.44 | 3.60 | 28.57 |
| Oxecta 7.5 mg | 0.13 | 0.6 | Not performed | Not performed |

TABLE 10G

Syringability and Extraction study on Oxycodone HCl Tablets in Vinegar (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 4.5 | 80.0 | Not needed; T0 exceeds Q value in Specifications | Not needed; T0 exceeds Q value in Specifications |
| Example 5A, 15 mg | 0.15 | 4.42 | 3.10 | 46.83 |
| Oxecta 7.5 mg | 0.1 | 0.7 | Not performed | Not performed |

TABLE 10H

Syringability and Extraction study on Oxycodone HCl Tablets in 40% EtOH (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 3.6 | 59.7 | Not needed; T0 exceeds Q value in Specifications | Not needed; T0 exceeds Q value in Specifications |
| Example 5A, 15 mg | 0.20 | 3.36 | 3.15 | 38.04 |
| Oxecta 7.5 mg | 0.1 | 0.1 | N/A | N/A |

TABLE 10I

Syringability and Extraction study on Oxycodone HCl Tablets in 0.9% Saline (n = 2)

| | T0 | | T10 | |
|---|---|---|---|---|
| Sample | Extraction volume (ml) | Oxycodone extracted (%) | Extraction volume (ml) | Oxycodone extracted (%) |
| Roxicodone 15 mg tablets (RLD) | 4.5 | 79.8 | Not needed; T0 exceeds Q value in Specifications | Not needed; T0 exceeds Q value in Specifications |
| Example 5A, 15 mg | 0.85 | 3.78 | 1.80 | 15.30 |

TABLE 10I-continued

Syringability and Extraction study on Oxycodone HCl Tablets in 0.9% Saline (n = 2)

| Sample | T0 | | T10 | |
|---|---|---|---|---|
| | Extraction volume (ml) | Oxycodone extracted (%) | Extraction volume (ml) | Oxycodone extracted (%) |
| Oxecta 7.5 mg | 0.1 | 0.4 | N/A | N/A |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

We claim:

1. A method of treating pain comprising administering to a patient in need thereof, an immediate release solid oral dosage form comprising a plurality of particles, each particle comprising:
   (i) a core comprising a substrate and an active agent selected from the group consisting of oxycodone, hydrocodone, naloxone and pharmaceutically acceptable salts thereof, and mixture thereof, wherein the active agent is layered over the substrate; and
   (ii) a material that is sensitive to acidic pH layered over the core, wherein the material is present in an amount of about 9% (w/w) to about 28% (w/w) and comprises a polyacrylate comprising a copolymer of methyl methacrylate, butyl methacrylate and dimethylaminoethyl methacrylate;
   wherein the plurality of particles are dispersed in a matrix comprising a gelling agent comprising pregelatinized starch, wherein the gelling agent is present in an amount ranging from about 0.25% (w/w) to about 10% (w/w),
   wherein a weight ratio of the material that is sensitive to acidic pH to the gelling agent is about 2.6:1 to about 13:1, and
   wherein the immediate release solid oral dosage form releases at least about 70% or more of the active agent within 45 minutes as measured by in-vitro dissolution in a USP Apparatus 2 (paddle) at 50 rpm in 500 ml 0.1 N HCl at 37° C.

2. The method of claim 1, wherein the matrix further comprises a disintegrant.

3. The method of claim 1, wherein the matrix further comprises a filler.

4. The method of claim 1, wherein the core comprises an inert excipient layered with the active agent.

5. The method of claim 1, wherein the plurality of particles are in the form of a granulation.

6. The method of claim 1, wherein the gelling agent further comprises a material selected from the group consisting of sugars, sugar derived alcohols, starch, starch derivatives, cellulose derivatives, attapulgites, bentonites, dextrins, alginates, carrageenan, gums, pectins, gelatin, kaolin, lecithin, magnesium aluminum silicate, carbomers, carbopols, polyvinylpyrrolidone, polyethylene glycol, polyethylene oxide, polyvinyl alcohol, silicon dioxide, curdlan, furcelleran, egg white powder, lacto albumin, soy protein, chitosan, surfactants, emulsifiers, hydroxyethylcellulose, guar gum, xanthan gum, alginate and mixtures thereof.

7. The method of claim 1, wherein the immediate release solid oral dosage form releases at least about 85% or more of the active agent within 45 minutes as measured by in-vitro dissolution in a USP Apparatus 2 (paddle) at 50 rpm in 500 ml 0.1 N HCl at 37° C.

8. The method of claim 1, wherein the immediate release solid oral dosage form releases at least about 85% or more of the active agent within 60 minutes as measured by in-vitro dissolution in a USP Apparatus 2 (paddle) at 50 rpm in 500 ml 0.1 N HCl at 37° C.

9. The method of claim 2, wherein the disintegrant is selected from the group consisting of cross-linked sodium carboxymethylcellulose, starch, sodium starch glycolate, cross-linked polyvinylpyrrolidone, crospovidone and mixtures thereof.

10. The method of claim 2, wherein the disintegrant is in an amount of about 0.2% (w/w) to about 25% (w/w) of the total dosage form.

11. The method of claim 3, wherein the filler is selected from the group consisting of a saccharide, sucrose, dextrose, lactose, fructose, mannitol, a cellulosic derivative, microcrystalline cellulose and combinations thereof.

12. The method of claim 3, wherein the filler is in an amount of about 15% (w/w) to about 95% (w/w) of the total dosage form.

13. The method of claim 1, wherein each particle has a mean diameter of about 0.1 mm to about 10 mm.

14. The method of claim 1, wherein the dosage form comprises about 2 to about 75 particles, or about 50 to about 500 particles.

15. The method of claim 1, wherein the substrate comprises an inert excipient or a non-opioid analgesic.

16. The method of claim 15, wherein the inert excipient is selected from the group consisting of a sugar sphere and a microcrystalline cellulose bead.

17. The method of claim 15, wherein the non-opioid analgesic is selected from the group consisting of acetaminophen, ibuprofen and aspirin.

18. The method of claim 1, wherein recovery of the drug is less than about 10% based on a syringeability test whereby the composition is subject to dissolution in 5 ml of water with agitation at room temperature for 30 seconds and the resultant solution is aspirated with a 27 1/2 gauge needle.

19. A method of treating pain comprising administering to a patient in need thereof, an immediate release solid oral dosage form comprising a tablet comprising a plurality of particles, each particle comprising:
   (i) a core comprising a substrate and a mixture of a drug, a disintegrant and an excipient, wherein the mixture is layered over the substrate, and wherein the drug is selected from a group consisting of about 2.5 mg to about 10 mg oxycodone hydrochloride, about 2.5 mg to about 15 mg hydrocodone bitartrate, about 6.1 mg naloxone hydrochloride and mixtures thereof; and
   (ii) a material that is sensitive to acidic pH layered over the core, wherein the material that is sensitive to acidic pH is present in an amount of about 9%% (w/w) to about 28%% (w/w) and comprises a polyacrylate comprising a copolymer of (i) methyl methacrylate and diethylaminoethyl methacrylate or (ii) methyl methacrylate, butyl methacrylate and dimethylaminoethyl methacrylate;
   wherein the plurality of particles are dispersed in a matrix comprising a gelling agent comprising pregelatinized starch, wherein the gelling agent is present in an amount ranging from about 0.25% (w/w) to about 10% (w/w), wherein a weight ratio of the material that is sensitive to acidic pH to the gelling agent is about 2.6:1 to about 13:1, and wherein the immediate release solid oral dosage form releases about 70% or more of the drug within 45 minutes as measured by in-vitro dissolution in a USP Apparatus 2 (paddle) at 50 rpm in 500 ml 0.1 N HCl at 37° C.

20. A method of treating pain comprising administering to a patient in need thereof, an immediate release solid oral dosage form comprising a tablet comprising a plurality of particles, each particle comprising:

(i) a core comprising a substrate and a drug selected from a group consisting of oxycodone hydrochloride, naloxone hydrochloride and mixtures thereof, wherein the drug is mixed with (a) a disintegrant comprising povidone and (b) an excipient comprising lactose monohydrate to form a mixture, and the mixture is layered over the substrate; and (ii) a material that is sensitive to acidic pH layered over the core, wherein the material that is sensitive to acidic pH is in an amount of about 9% (w/w) to about 28% (w/w), the material that is sensitive to acidic pH comprising a polyacrylate comprising a copolymer of (i) methyl methacrylate and diethylaminoethyl methacrylate or (ii) methyl methacrylate, butyl methacrylate and dimethylaminoethyl methacrylate;

wherein the plurality of particles are dispersed in a matrix comprising a gelling agent comprising pregelatinized starch, wherein the gelling agent is in an amount from about 0.25% (w/w) to about 10% (w/w), wherein a weight ratio of the material that is sensitive to acidic pH to the gelling agent is about 2.6:1 to about 13:1, and wherein the immediate release solid oral dosage form releases about 70% or more of the drug within 45 minutes as measured by in-vitro dissolution in a USP Apparatus 2 (paddle) at 50 rpm in 500 ml 0.1 N HCl at 37° C.

21. The method of claim 20, wherein the material that is sensitive to acidic pH comprises the copolymer of methyl methacrylate, butyl methacrylate and dimethylaminoe thyl methacrylate.

22. The method of claim 20, wherein the immediate release solid oral dosage form comprises a surfactant.

23. A method of treating pain comprising administering to a patient in need thereof, an immediate release solid oral dosage form comprising a tablet comprising a plurality of particles, each particle comprising:

(i) a core comprising oxycodone or a pharmaceutically acceptable salt thereof, wherein the oxycodone or pharmaceutically acceptable salt thereof is layered over the substrate; and (ii) a material that is sensitive to acidic pH layered over the core, wherein the material is present in an amount of about 9% (w/w) to about 28% (w/w) and comprises a polyacrylate comprising a copolymer of methyl methacrylate, butyl methacrylate and dimethylaminoethyl methacrylate;

wherein the plurality of particles are dispersed in a matrix comprising a gelling agent, the gelling agent comprising pregelatinized starch, wherein the gelling agent is present in an amount ranging from about 0.25% (w/w) to about 10% (w/w), wherein a weight ratio of the material that is sensitive to acidic pH to the gelling agent is about 2.6:1 to about 13:1, and wherein the immediate release solid oral dosage form releases about 70% or more of the drug within 45 minutes as measured by in-vitro dissolution in a USP Apparatus 2 (paddle) at 50 rpm in 500 ml 0.1 N HCl at 37° C.

* * * * *